(12) United States Patent
Jaen et al.

(10) Patent No.: US 6,649,593 B1
(45) Date of Patent: Nov. 18, 2003

(54) MODULATORS OF SREBP PROCESSING

(75) Inventors: Juan C. Jaen, Burlingame, CA (US); Leping Li, Burlingame, CA (US); Michael S. Brown, Dallas, TX (US); Joseph L. Goldstein, Dallas, TX (US); Dong Cheng, Hockessin, DE (US)

(73) Assignees: Tularik Inc., So. San Francisco, CA (US); Board of Regents, University of Texas Systems, Dallas, TX (US)

( * ) Notice: Subject to any disclaimer, the term of this patent is extended or adjusted under 35 U.S.C. 154(b) by 58 days.

(21) Appl. No.: 09/680,571

(22) Filed: Oct. 6, 2000

Related U.S. Application Data

(60) Provisional application No. 60/159,236, filed on Oct. 13, 1999.

(51) Int. Cl.$^7$ .......................... A61K 38/06; C07K 5/087
(52) U.S. Cl. ........................................ 514/18; 530/331
(58) Field of Search .............................. 514/15, 16, 17, 514/18, 19; 530/328, 329, 330, 331

(56) References Cited

U.S. PATENT DOCUMENTS

| | | | | |
|---|---|---|---|---|
| 4,499,082 A | * | 2/1985 | Shenvi et al. ................... 260/1 |
| 4,548,926 A | * | 10/1985 | Matsueda et al. ............. 514/18 |
| 4,589,926 A | * | 5/1986 | Holmstrand ................ 134/109 |
| 4,644,055 A | * | 2/1987 | Kettner et al. ............... 530/324 |
| 4,963,655 A | * | 10/1990 | Kinder et al. ............... 530/331 |
| 4,997,950 A | * | 3/1991 | Murphy et al. .......... 548/304.1 |
| 5,101,068 A | * | 3/1992 | Palmer ....................... 556/429 |
| 5,187,157 A | * | 2/1993 | Kettner et al. ................. 514/18 |
| 5,338,726 A | * | 8/1994 | Shiosaki et al. .............. 514/17 |
| 5,431,842 A | * | 7/1995 | Panandiker et al. ........ 264/189 |
| 5,444,042 A | * | 8/1995 | Bartus et al. ................ 435/184 |
| 5,496,927 A | * | 3/1996 | Kolb et al. .................. 530/328 |
| 5,498,793 A | * | 3/1996 | Sohda et al. ................ 548/493 |
| 5,541,290 A | * | 7/1996 | Harbeson et al. ........... 530/330 |
| 5,605,826 A | * | 2/1997 | Wright et al. ............... 435/212 |
| 5,650,508 A | * | 7/1997 | Powers ....................... 544/168 |
| 5,663,171 A | * | 9/1997 | Chen et al. .................. 514/19 |
| 5,714,471 A | * | 2/1998 | Rowe et al. ............... 435/7.21 |
| 5,804,560 A | * | 9/1998 | McDonald et al. ........... 514/19 |
| 5,831,068 A | * | 11/1998 | Nair et al. ................. 424/278.1 |
| 5,834,588 A | * | 11/1998 | Wasserman et al. ........ 530/333 |
| 5,851,985 A | * | 12/1998 | Tepic et al. .............. 210/195.2 |
| 5,876,945 A | * | 3/1999 | Chisholm et al. ........... 435/219 |
| 6,034,066 A | * | 3/2000 | Johnson et al. ............... 514/18 |
| 6,083,903 A | * | 7/2000 | Adams et al. .................. 514/2 |
| 6,084,065 A | * | 7/2000 | Camaggi et al. ............ 530/331 |
| 6,096,711 A | * | 8/2000 | Sherman et al. ............ 436/173 |
| 6,180,586 B1 | * | 1/2001 | Saunders et al. ........... 510/320 |
| 6,235,717 B1 | * | 5/2001 | Leban et al. .................. 514/18 |
| 6,291,640 B1 | * | 9/2001 | Bailey et al. ............... 530/330 |
| 6,322,962 B1 | * | 11/2001 | Brown et al. ............ 435/320.1 |
| 6,329,148 B1 | * | 12/2001 | Rosen et al. .................... 435/6 |

FOREIGN PATENT DOCUMENTS

| | | | | |
|---|---|---|---|---|
| WO | WO94/25049 | 11/1994 | | |
| WO | WO00/09677 | 2/2000 | | |
| WO | WO00/26348 | 5/2000 | | |
| WO | WO 200056760 A1 | * | 9/2000 | ......... A61K/31/198 |

OTHER PUBLICATIONS

Cheng, Dong et al., "Secreted Site–1 Protease Cleaves Peptides Corresponding to Luminal Loop of Sterol Regulatory Element–Binding Proteins", *The Journal of Biological Chemistry*, 274(32):22805–22812 (1999).

Espenshade, Peter J. et al., "Autocatalytic Processing of Site–1 Protease Removes Propeptide and Permits Cleavage of Sterol Regulatory Element–binding Proteins", *The Journal of Biological Chemistry*, 274(32):22795–22804 (1999).

Seidah, Nabil G. et al., "Mammalian subtilisin/kexin isozyme SKI–1: A widely expressed proprotein convertase with a unique cleavage specificity and cellular localization", *Proc. Natl. Acad. Sci. USA*, 96:1321–1326 (1999).

Demuth, Hans–Ulrich, "Recent Developments in Inhibiting Cysteine and Serine Proteases", *Journal of Enzyme Inhibition*, 3:249–278 (1990).

Imperiali, Barbara et al., "Inhibition of Serine Proteases by Peptidyl Fluoromethyl Ketones", *Biochemistry*, 25:3760–3767 (1986).

Shepherd, Timothy A. et al., "Small Peptidic Aldehyde Inhibitors of Human Rhinovirus 3C Protease", *Bioorganic & Medicinal Chemistry Letters*, 6(23):2893–2896 (1996).

Siezen, Roland J. et al., "Subtilases: The superfamily of subtilisin–like serine proteases", *Protein Science*, 6:501–523 (1997).

* cited by examiner

*Primary Examiner*—Jon P. Weber
(74) *Attorney, Agent, or Firm*—Townsend and Townsend and Crew LLP

(57) ABSTRACT

Compounds, compositions and methods are provided for the inhibition of S1 protease and for the modulation of cholesterol homeostasis in a cell.

12 Claims, No Drawings

MODULATORS OF SREBP PROCESSING

CROSS-REFERENCES TO RELATED APPLICATIONS

This application claims the benefit of U.S. Provisional Application Serial No. 60/159,236, filed Oct. 13, 1999, the disclosure of which is incorporated by reference.

STATEMENT AS TO RIGHTS TO INVENTIONS MADE UNDER FEDERALLY SPONSORED RESEARCH AND DEVELOPMENT

A portion of the present invention was made under federally sponsored research and development grant number HL-20948 from the National Institutes of Health. The Government may have rights in certain aspects of this invention.

BACKGROUND OF THE INVENTION

The lipid composition of animal cells is controlled by transcriptions factors known as sterol regulatory element binding proteins (SREBPs). These transcription factors are bound to membranes of the endoplasmic reticulum (ER) and nuclear envelope, and are released by sterol-regulated proteolysis. SREBP release is initiated by Site-1protease (S1P), which cleaves SREBPs in the ER luminal loop between two membrane spanning regions (see, for example, Sakai, et al., Cell 85:1037–1046 (1996); Duncan, et al., *J. Biol. Chem.* 272:12778–12785 (1997); and copending application Ser. No. 09/360,237, entitled "cDNA Cloning of Site-1 Protease for SREBPs").

S1P has features characteristic of a superfamily of serine proteases, broadly characterized as subtilisins, which are found in all living organisms from bacteria to humans (see Siezen and Leunissen, *Prot. Sci.* 6:501–523 (1997)). Human S1P consists of about 1052 amino acids. Based on its resemblance to other serine proteases, it has been postulated that the catalytic triad should consist of Asp218, His249 and Ser414 (ibid.). Additionally, the S1P sequence consists of six potential sites of N-linked glycosylation, an unbroken stretch of 25 nonpolar residues near the carboxy terminus (consistent with a membrane-spanning sequence), and a COOH terminal sequence of 30 amino acids that is strikingly rich in prolines and basic residues (including a complete absence of acidic residues).

From a functional viewpoint, the action of S1P most resembles that of the furins, which are subtilases of the Kex2p-like subfamily that process proteins such as the insulin pro-receptor and pro-endothelin-1. S1P differs from the furins in two respects: (1) substrate recognition (furins always cleave after dibasic residues and S1P may cleave after nonbasic residues, such as cleavage after the RSVL (SEQ ID NO:1) sequence; and (2) cellular location (furins act in post-Golgi secretory vesicles, and S1P acts in a pre-Golgi compartment, thought to be the ER). If S1P does function in the ER, its activity must be regulated so as to prevent it from degrading nascent polypeptides nonspecifically.

In view of the role of S1P in regulating SREBPs, and thereby regulating the synthesis of fatty acids and cholesterol, there exists a need for compounds that can inhibit the activity of S1P. The present invention provides such compounds, as well as methods for the modulation of cholesterol homeostasis in animal cells.

SUMMARY OF THE INVENTION

The present invention provides compounds, compositions and methods useful for inhibiting of S1 protease, and for modulating cholesterol homeostasis in cells. The compounds provided herein, and which are useful in the present compositions and methods are those having the formula:

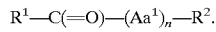

$$R^1-C(=O)-(Aa^1)_n-R^2.$$

In the general formula above, the symbol $R^1$ represents $(C_1-C_6)$alkyl, aryl$(C_1-C_6)$alkyl, aryl, $(C_1-C_6)$alkylamino, aryl$(C_1-C_6)$alkylamino, $(C_1-C_6)$alkoxy, or aryl$(C_1-C_6)$alkoxy.

The symbol Aa represents a divalent amino acid residue, connected via its amino and acyl groups, or a linking group. The superscript i is an integer denoting the position downstream from —C(=O)— and the subscript n is an integer of from 2 to 10, such that Aa at any position can be the same as or different from Aa at any other position, with the proviso that at least two of Aa are amino acid residues.

The symbol $R^2$ represents any one of:

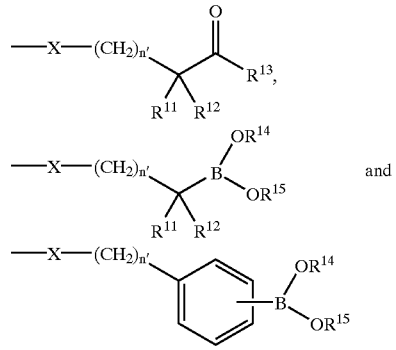

and in which X is O, NH or N—$(C_1-C_4)$alkyl and the subscript n' is an integer of from 0 to 4. Additionally, the symbols $R^{11}$ and $R^{12}$ independently represent H, $(C_1-C_8)$alkyl, aryl, or aryl$(C_1-C_6)$alkyl, or taken together, $R^{11}$ and $R^{12}$ form a five- to seven-membered ring; $R^{13}$ represents H, $CF_3$, $CH_2Y$, heteroaryl, $CONHR^{16}$ and $CO_2R^{16}$; wherein Y is a leaving group and $R^{16}$ is H or $(C_1-C_4)$alkyl. The symbols $R^{14}$ and $R^{15}$ independently represent H, $(C_1-C_6)$alkyl, aryl, and aryl$(C_1-C_6)$alkyl; or taken together, $R^{14}$ and $R^{15}$ form a five- to seven-membered ring.

BRIEF DESCRIPTION OF THE DRAWINGS

Not applicable

DESCRIPTION OF THE SPECIFIC EMBODIMENTS

Abbreviations and Definitions

The following abbreviations are used herein:

Ac, acetyl; AMC, 7-amino-4-methylcoumarin; ALLN, N-acetyl-leucinal-leucinal-norleucinal; Bn, benzyl; BOC, t-butyloxycarbonyl; Cbz, benzyloxycarbonyl; CHO, Chinese hamster ovary; CMV, cytomegalovirus; DMSO: dimethylsulfoxide; $Et_3N$, triethylamine; Fmoc, fluorenylmethoxy; MCA, 4-methyl-coumaryl-7-amide; MeOH, methanol; S1P, Site 1 protease; SREBP, sterol regulatory element-binding protein; and TFA, trifluoroacetic acid.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1-C_{10}$ means one to ten carbon atoms). Examples of saturated hydrocarbon alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl." Alkyl groups which are limited to hydrocarbon groups are termed "homoalkyl".

The term "alkylene" by itself or as part of another substituent means a divalent radical derived from an alkane, as exemplified by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$—and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl,tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quaternized. The aryl groups that contain heteroatoms may be referred to as "heteroaryl" and can be attached to the remainder of the molecule through a heteroatom. Non-limiting examples of aryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below.

The term "arylalkyl" is meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a van ety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R'" each independently refer to hydrogen, unsubstituted ($C_1$–$C_8$)alkyl and heteroalkyl, unsubstituted aryl, aryl substituted with 1–3 halogens, unsubstituted alkyl, alkoxy or thioalkoxy groups, or aryl-($C_1$–$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similarly, substituents for the aryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$–C$_4$)alkoxy, and perfluoro(C$_1$–C$_4$)alkyl, in a number ranging from zero to the total number of open valences on the aromatic ring system; and where R', R" and R'" are independently selected from hydrogen, (C$_1$–C$_8$)alkyl and heteroalkyl, unsubstituted aryl, (unsubstituted aryl)-(C$_1$–C$_4$)alkyl, and (unsubstituted aryl)oxy-(C$_1$–C$_4$)alkyl.

Two of the substituents on adjacent atoms of the aryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$–C$_6$)alkyl.

As used herein, the term "heteroatom" is meant to include oxygen (O), nitrogen (N), sulfur (S) and silicon (Si).

For the compounds of the present invention which contain amino acid or peptide fragments, the amino acid residues may be those 20 L-α-amino acids genetically encoded or any other fragments that contain a primary or secondary amine and a free carboxylic acid. The conventional single-letter and three-letter designations for gene-encoded amino acids are as follows:

| Amino Acid | One-Letter Symbol | Three-Letter Symbol |
| --- | --- | --- |
| Alanine | A | Ala |
| Arginine | R | Arg |
| Asparagine | N | Asn |
| Aspartic Acid | D | Asp |
| Cysteine | C | Cys |
| Glutamine | Q | Gln |
| Glutamic Acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Commonly encountered amino acids which are not gene-encoded may also be used in the present invention. These amino acids and their abbreviations include ornithine (Orn); t-butylglycine (t-BuG); phenylglycine (PhG); cyclohexyla-lanine (Cha); norleucine (Nle); 2-naphthylalanine (2-Nal), 1-naphthylalanine (1-Nal); 2-thienylalanine (2-Thi); 1,2,3,4-tetrahydroisoquinoline-3-carboxylic acid (Tic); N-methylisoleucine (N-MeIle); homoarginine (Har); Nα-methylarginine (N-MeArg) and sarcosine (Sar).

All of the amino acids used in the present invention may be either the D- or L-isomer. The L-isomers are preferred. One of skill in the art will understand that in the process of connecting amino acid fragments together a molecule of water is removed, such that contiguous amino acid residues are connected by amide linkages generated from the carboxylic acid of one residue and the amino group of the other residue.

The term "linking group" is meant to include either a covalent single or double bond, or a group capable of covalently attaching or connecting two radicals. Examples of linking groups are alkylene, alkyleneoxy, alkyleneamino, alkylenediamino, alkylenedioxy, and the like. Further, linking groups such as (C$_1$–C$_6$)alkyleneoxy is meant to include —CH$_2$CH$_2$CH$_2$O—, —CH$_2$CH$_2$CH$_2$CH$_2$O—, and —CH$_2$CH$_2$CH$_2$CH$_2$CH$_2$CH$_2$O—,as well as branched linking groups and those groups in which one or more methylene groups have been replaced by heteroatoms (e.g., —CH$_2$OCH$_2$CH$_2$O— and —CH$_2$CH$_2$NHCH$_2$CH$_2$CH$_2$O—). Linking groups containing "dioxy" and "diamino" are meant to include those alkylene linking groups having oxygen atoms and amino groups at each termini, respectively.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Description of the Embodiments

I. Compounds That Modulate SREBP Processing

In one aspect, the present invention provides compounds that are useful as modulators of SREBP processing. The ability of the compounds provided herein to modulate SREBP processing also supports the compounds use for the modulation of cholesterol homeostasis in cells. The compounds are represented by the formula:

$$R^1\text{—C(=O)—}(Aa^1)_n\text{—}R^2. \quad (I)$$

In the general formula above, the symbol $R^1$ represents $(C_1-C_6)$alkyl, aryl$(C_1-C_6)$alkyl, aryl, $(C_1-C_6)$alkylamino, aryl$(C_1-C_6)$alkylamino, $(C_1-C_6)$alkoxy, or aryl$(C_1-C_6)$alkoxy. In preferred embodiments, $R^1$ is $(C_1-C_6)$alkyl, aryl $(C_1-C_6)$alkyl, $(C_1-C_6)$alkylamino, $(C_1-C_6)$alkoxy, or aryl $(C_1-C_6)$alkoxy. Further preferred are those embodiments in which $R^1$ is $(C_1-C_3)$alkyl, aryl$(C_1-C_3)$alkyl, $(C_1-C_6)$alkoxy, or aryl$(C_1-C_6)$alkoxy. Most preferred are those embodiments in which $R^1$ is $(C_1-C_3)$alkyl, aryl$(C_1-C_3)$alkyl, $(C_1-C_3)$alkoxy, or aryl$(C_1-C_3)$alkoxy. Exemplary of the most preferred group for $R^1$ are methoxy, ethoxy, methyl, ethyl, benzyl, phenethyl, benzyloxy and phenylethoxy.

The symbol Aa represents a divalent amino acid residue or a linking group. The superscript i is an integer denoting the position downstream from —C(=O)— and the subscript n is an integer of from 2 to 10, such that Aa at any position can be the same as or different from Aa at any other position, with the proviso that at least two of Aa are amino acid residues. A variety of linking groups are useful as Aa components, typically to provide spacing between certain of the amino acid residues, or spacing between an amino acid residue and either terminus of the compound. In particular, the linking groups will be selected from a single or double bond, $(C_1-C_6)$alkylene, $(C_1-C_6)$alkylenoxy, $(C_1-C_6)$ alkylenamino, $(C_1-C_6)$alkylenedioxy, and $(C_1-C_6)$ alkylenediamino. Each of these linking groups is further meant to include heteroalkylene versions, for example, —$CH_2CH_2OCH_2CH_2$—.

Amino acids useful in the present invention include naturally-occurring gene-encoded L-α-amino acids, the corresponding D-isomers, and commonly encountered non-gene-encoded amino acids (for example, phenylglycine, t-butylglycine, homoarginine, β-alanine, and the like). Additionally, each of the amino acids can be further substituted. For example, one group of amino acids useful in the present invention include 3-(amidino)phenylglycine, 4-(amidino)phenylglycine, 3-(amidino)phenylalanine, 4-(amidino)phenylalanine, 3-(guanidino)phenylglycine, 4-(guanidino)phenylglycine, 3-(guanidino)phenylalanine and 4-(guanidino)phenylalanine. Other substituents are also useful for certain of the amino acids and can be selected from the group of substituents provided above for alkyl groups and aryl groups.

In preferred embodiments, -$(Aa^1)_n$- is a peptide fragment of from two to ten amino acid residues, for example, -$Aa^1$-$Aa^2$-, -$Aa^1$-$Aa^2$-$Aa^3$-, -$Aa^1$-$Aa^2$-$Aa^3$-$Aa^4$-$Aa^5$-, -$Aa^1$-$Aa^2$-$Aa^3$-$Aa^4$-$Aa^5$-$Aa^6$-$Aa^7$-, and the like. In each of these peptide fragments, the individual amino acids can be the same or different, and can be any of the amino acids noted above. Particularly preferred are compounds in which -$(Aa^1)_n$ represents a tripeptide fragment. Further preferred are those compounds in which -$(Aa^1)_n$ represents a tripeptide fragment wherein $Aa^1$ is Lys, Arg or a divalent amino acid residue of the formula:

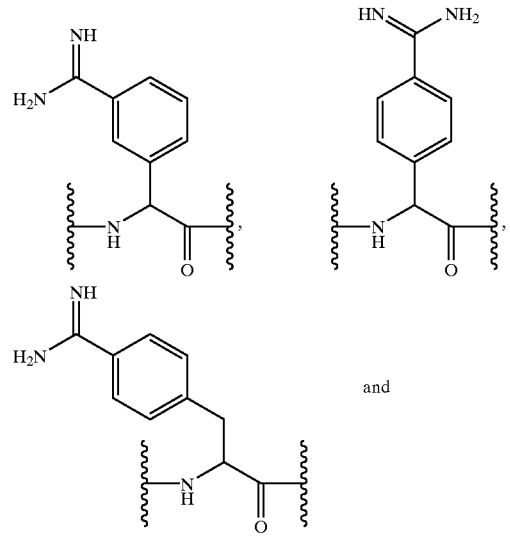

-continued

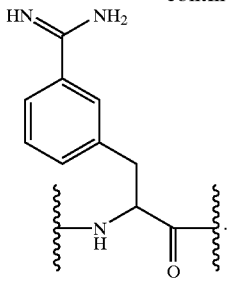

Still further preferred are those compounds in which -(Aa$^1$)$_n$- is a tripeptide fragment in which Aa$^1$ is Lys or Arg (K or R). Also preferred, are those embodiments in which -(Aa$^1$)$_n$- is a tripeptide fragment wherein Aa$^2$ is Ser, Arg or Asn (S, R or N) and Aa$^3$ is Met, Val or Leu (M, V or L).

Returning to formula I above, the symbol R$^2$ represents any one of:

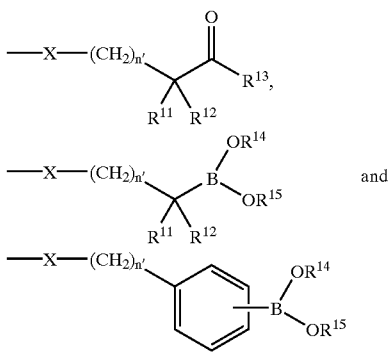

in which X is O, NH or N—(C$_1$–C$_4$)alkyl and the subscript n' is an integer of from 0 to 4. Additionally, the symbols R$^{11}$ and R$^{12}$ independently represent H, (C$_1$–C$_8$)alkyl, aryl, or aryl(C$_1$–C$_6$)alkyl, or taken together R$^{11}$ and R$^{12}$ form a five- to seven-membered ring. The symbol R$^{13}$ represents H, CF$_3$, CH$_2$Y, heteroaryl, CONHR$^{16}$ and CO$_2$R$^{16}$; wherein Y is a leaving group and R$^{16}$ is H or (C$_1$–C$_4$)alkyl. A variety of leaving groups are useful in this component of the invention including, halogen atoms, triflate esters, tosylate esters, mesylate esters, and the like. Similarly, a variety of heteroaryl groups are useful including thiazolyl, oxazolyl, benzthiazolyl and benzoxazolyl groups. The symbols R$^{14}$ and R$^{15}$ independently represent H, (C$_1$–C$_6$)alkyl, aryl, and aryl(C$_1$–C$_6$)alkyl; or taken together, R$^{14}$ and R$^{15}$ form a five- to seven-membered ring.

In preferred embodiments, R$^2$ is a radical selected from

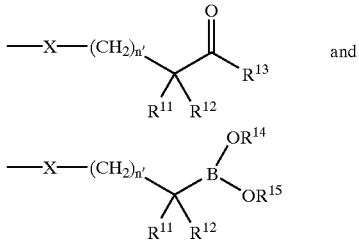

in which X is NH; n' is 0 or 1; R$^{11}$, R$^{14}$ and R$^{15}$ are each H; R$^{12}$ is (C$_1$–C$_4$)alkyl, (C$_2$–C$_8$)heteroalkyl or aryl(C$_1$–C$_2$)alkyl; and R$^{13}$ is H, CH$_2$Cl, CH$_2$F, CF$_3$, heteroaryl, CO$_2$R$^{16}$ or CONHR$^{16}$.

Still further preferred are those embodiments in which R$^2$ is a radical of the formula:

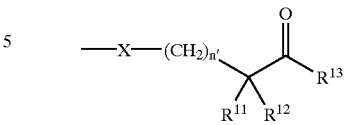

in which X is NH; n' is 0; R$^{11}$ is H; R$^{12}$ is 2-methyl-1-propyl, methyl, benzyl, 4-amino-1-butyl or 3-guanidino-1-propyl; and R$^{13}$ is a member selected from the group consisting of H, CH$_2$Cl, CH$_2$F, CF$_3$, CONHEt, CO$_2$Et, 2-benzothiazolyl and 2-thiazolyl.

In one group of particularly preferred embodiments, the compounds of the present invention are represented by their more conventional amino acid formulae as: Ac-RSVL-H (SEQ ID NO:2), Ac-RSVL-CH$_2$Cl (SEQ ID NO:3), Ac-RSVL-CH$_2$F (SEQ ID NO:4), Ac-RSVL-CF$_3$ (SEQ ID NO:5), Ac-RSVL-CONHEt (SEQ ID NO :6), Ac-RSVL-CO$_2$Et (SEQ ID NO:7), Ac-RSVL-2-thiazolyl (SEQ ID NO:8), Ac-RSVL-2-benzothiazolyl (SEQ ID NO:9), Ac-RSLL-H (SEQ ID NO:10), Ac-RSLL-CH$_2$Cl (SEQ ID NO:11), Ac-RSLL-CH$_2$F (SEQ ID NO:12), Ac-RSLL-CF$_3$ (SEQ ID NO:13), Ac-RSLL-CONHEt (SEQ ID NO:14), Ac-RSLL-CO$_2$Et (SEQ ID NO:15), Ac-RSLL-2-benzothiazolyl (SEQ ID NO:16), Ac-RSLL-2-thiazolyl (SEQ ID NO:17), Ac-RSLK-H (SEQ ID NO:18), Ac-RSLK-CH$_2$Cl (SEQ ID NO:19), Ac-RSLK-CH$_2$F (SEQ ID NO:20), Ac-RSLK-CF$_3$ (SEQ ID NO:21), Ac-RSLK-CONHEt (SEQ ID NO:22), Ac-RSLK-CO$_2$Et (SEQ ID NO:23), Ac-RSLK-2-thiazolyl (SEQ ID NO:24), Ac-RSLK-2-benzothiazolyl (SEQ ID NO:25), Ac-KSVL-H (SEQ ID NO:26), Ac-KSVL-CH$_2$Cl (SEQ ID NO:27), Ac-KSVL-CH$_2$F (SEQ ID NO:28), Ac-KSVL-CF$_3$ (SEQ ID NO:29), Ac-KSVL-CONHEt (SEQ ID NO:30), Ac-KSVL-CO$_2$Et (SEQ ID NO:31), Ac-KSVL-2-benzothiazolyl (SEQ ID NO:32), Ac-KSVL-2-thiazolyl (SEQ ID NO:33), Ac-RSVK-H (SEQ ID NO:34), Ac-RSVK-CH$_2$F (SEQ ID NO:35), Ac-RSVK-CH$_2$Cl (SEQ ID NO:36), Ac-RSVK-CF$_3$ (SEQ ID NO:37), Ac-RSVK-CONHEt (SEQ ID NO:38), Ac-RSVK-CO$_2$Et (SEQ ID NO:39), Ac-RSVK-2-benzothiazolyl (SEQ ID NO:40) and Ac-RSVK-2-thiazolyl (SEQ ID NO:41).

In another group of particularly preferred embodiments, the compounds of the present invention are represented by: Cbz-RSVL-H (SEQ ID NO:42), Cbz-RSVL-CH$_2$F (SEQ ID NO:43), Cbz-RSVL-CH$_2$Cl (SEQ ID NO:44), Cbz-RSVL-CF$_3$ (SEQ ID NO:45), Cbz-RSVL-CONHEt (SEQ ID NO:46), Cbz-RSVL-CO$_2$Et (SEQ ID NO:47), Cbz-RSVL-2-thiazolyl (SEQ ID NO:48), Cbz-RSVL-2-benzothiazolyl (SEQ ID NO:49), Cbz-RSLL-H (SEQ ID NO:50), Cbz-RSLL-CH$_2$F (SEQ ID NO:51), Cbz-RSLL-CH$_2$Cl (SEQ ID NO:52), Cbz-RSLL-CF$_3$ (SEQ ID NO:53), Cbz-RSLL-CONHEt (SEQ ID NO:54), Cbz-RSLL-CO$_2$Et (SEQ ID NO:55), Cbz-RSLL-2-thiazolyl (SEQ ID NO:56), Cbz-RSLL-2-benzothiazolyl (SEQ ID NO:57), Cbz-RSLK-H (SEQ ID NO:58), Cbz-RSLK-CH$_2$F (SEQ ID NO:59), Cbz-RSLK-CH$_2$Cl (SEQ ID NO:60), Cbz-RSLK-CF$_3$ (SEQ ID NO:61), Cbz-RSLK-CONHEt (SEQ ID NO:62), Cbz-RSLK-CO$_2$Et (SEQ ID NO:64), Cbz-RSLK-2-thiazolyl (SEQ ID NO:65), Cbz-RSLK-2-benzothiazolyl (SEQ ID NO:66), Cbz-KSVL-H (SEQ ID NO:67), Cbz-KSVL-CH$_2$F (SEQ ID NO:68), Cbz-KSVL-CH$_2$Cl (SEQ ID NO:69), Cbz-KSVL-CF$_3$ (SEQ ID NO:69), Cbz-KSVL-CONHEt (SEQ ID NO:70), Cbz-KSVL-CO$_2$Et (SEQ ID NO:71), Cbz-KSVL-2-thiazolyl (SEQ ID NO:72), Cbz-KSVL-2-benzothiazolyl (SEQ ID NO:73), Cbz-RSVK-H (SEQ ID NO:74), Cbz-RSVK-CH$_2$F (SEQ ID NO:75), Cbz-RSVK-CH$_2$Cl (SEQ ID NO:76), Cbz-RSVK-CF$_3$ (SEQ ID NO:77), Cbz-RSVK-CONHEt (SEQ ID NO:78), Cbz-RSVK-CO$_2$Et (SEQ ID NO:79), Cbz-RSVK-2-thiazolyl (SEQ ID NO:80) and Cbz-RSVK-2-benzothiazolyl (SEQ ID NO:81).

In each of the above groups of tetrapeptide formulae, the symbol Ac is used in a conventional manner to depict an acetyl group attached at the N-terminus of the peptide fragment. Similarly, Cbz is used to depict a benzyloxycarbonyl group. Each of the groups provided at the C-terminus is attached directly to the carbonyl moiety of the C-terminal amino acid residue. Accordingly, when combined with the peptide formula, —H represents a terminal aldehyde functional group; —CH$_2$Cl represents a terminal chloromethylketone functional group; and —CONHEt represents a terminal N-ethyl α-ketoamide functional group.

A. Preparation of Compounds

Compounds of the present invention can be prepared using readily available starting materials or known intermediates. Scheme 1 provides synthesis avenues for the production of the subject compounds. One of skill in the art will understand that additional methods are also useful.

peptide fragments for some embodiments of the invention) used for coupling to a V-R$^2$ moiety (shown in Scheme 1 as ii) is synthesized either by the solution phase protocol where the C-terminal is orthogonally protected as an ester or by the standard solid phase Fmoc/t-Bu chemistry using a trityl or oxime resin. Both methods enable the selective unmasking of the C-terminal available for coupling to the Aa$^3$-R$^2$ subunit while leaving the side chain protections untouched to allow for further functional group manipulations.

Synthetic methods useful for the preparation of amino acid derivatives (R$^2$ subunits, or i in Scheme 1) can be found in the following references: chloromethylketones, see (a) Powers, et al., *J. Am. Chem. Soc.* 1970, 92, 1782–1783, (b) Chen, et al., *Tetrahedron Lett.* 1997, 38, 3175–3168, and (c) Teno, et al., *Chem. Pharm. Bull.* 1993, 41, 1079–1090; trifluoromethylketones, see Imperiali, et al., *Biochemistry*, 1986, 25, 3760; α-ketoheterocycles, see, (a) Edwards, et al., *J. Am. Chem. Soc.* 1992, 114, 1854, (b) Edwards, et al., *J. Med. Chem.* 1995, 38, 76–85, (c) Tsutsumi, et al., *Bioorg. Med. Chem. Lett.* 1994, 4, 831, (d) Tsutsumi, et al., *J. Med. Chem.* 1994, 37, 3492, (e) Costanzo, et al., *J. Med. Chem.* 1996, 39, 3039, (f) Akiyama, et al., *Bioorg. Med. Chem. Lett.*

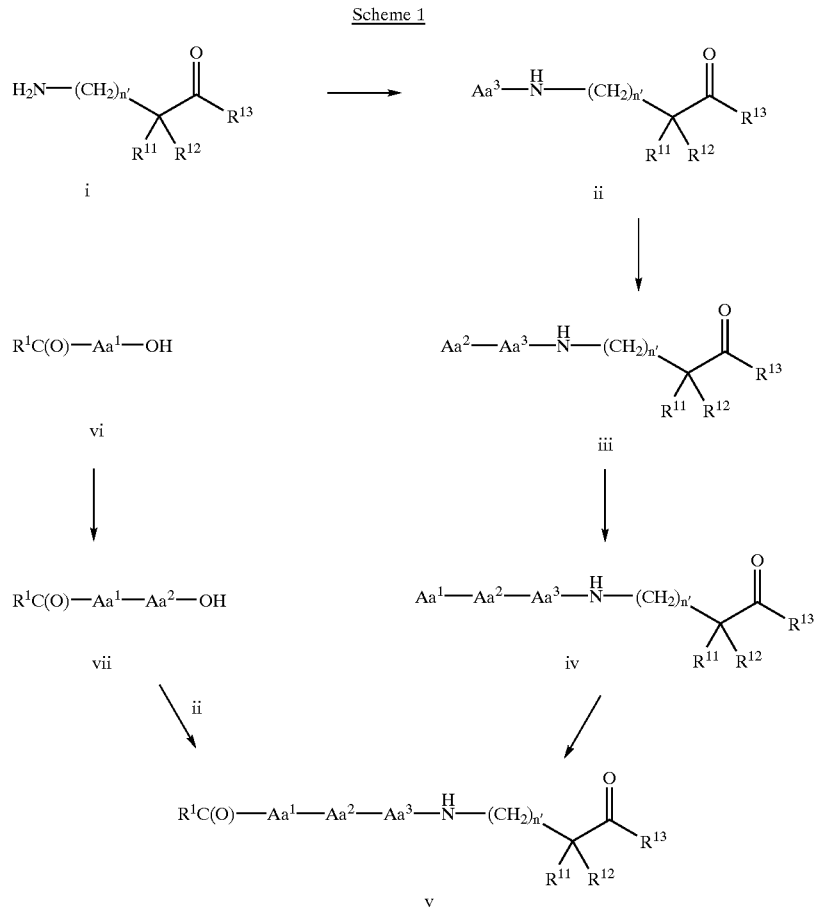

Scheme 1

Briefly, the claimed compounds can be assembled in a linear fashion employing the standard Fmoc/t-Bu and Boc/Bn protocols with minor modifications of the protection schemes and the reaction conditions (e.g., i→ii→iii→iv→v). More conveniently, these compounds can be synthesized by a convergent method (e.g., vi→vii→v). The peptide segment (for example, Ac-RS-OH, or longer 1997, 7, 533–538, and (g) Tamura, et al., *Bioorg. Med. Chem. Lett.* 1997, 7, 1359–1364; α-ketoamides, see, (a) Peet, et al., *J. Med. Chem.* 1990, 33, 394–407, (b) Iwanowicz, et al., *Bioorg. Med. Chem. Lett.* 1992, 2, 1607–1612, (c) Brady, et al., *Bioorg. Med. Chem.* 1995, 3, 1063–1078, and (d) Lewis, et al, *J. BioL. Chem.* 1998, 273, 4843–4854; diketoesters, see (a) Wasserman, et al., *Tetra-* hedron Lett. 1992, 33, 6003, and (b) Wasserman, et al., *Tetrahedron Lett.* 1990, 31, 5205; boronic acids, see (a) Matteson, et al., *J. Am. Chem. Soc.* 1981, 103, 5241, (b) Kettner, et al., *J. BioL. Chem.* 1984, 259, 15016, (c) Adams, et al., *Bioorg. Med. Chem. Lett.* 1998, 8, 333–338, and (d) Weber, et al., *Biochemistry* 1994, 34, 3750–3757.

The following exemplary procedures are meant to illustrate the preparation of selected components used in the present invention.

Leu-CH$_2$Cl, Hydrochloride Salt

Boc-Leu-OH (0.25 mmol) is treated with ethyl chloroformate (0.25 mmol) and Et$_3$N (0.25 mmol) in THF (10 mL) at −15° C. for 20 min. To this freshly formed mixed anhydride is added an etheral solution of diazomethane (prepared from nitrosomethylurea (1mmol)) at −15° C. and the mixture is stirred at 4° C. for 5 h. After addition of 7N HCl/dioxane (1 mmol) at −15° C., the reaction mixture is stirred at the same temperature for 3 h and the pH of the solution is adjusted to 7 with Et$_3$N. The solvent is removed by evaporation and the residue is extracted with AcOEt. The extract is washed with 10% citric acid, 5% Na$_2$CO$_3$ and water, dried over Na$_2$SO$_4$ and concentrated. The crude product is purified by chromatography on silica gel eluted with CHCl$_3$. The product is further purified by recrystalization from CHCl$_3$ and hexanes.

A solution of Boc-Leu-CH$_2$Cl (1 mmol) is treated with 7N HCl/dioxane (10 mmol) at room temperature for 60 min. Ether is then added to the solution to form a precipitate, which is collected by filtration and dried over KOH pellets in vacuo. Various chloromethylketones can be made from the esters of the corresponding Boc protected amino acids following procedures reported in the literature (see, for example, Chen, et al., *Tetrahedron Lett.*, 38:3175–3168 (1997)).

Preparation of Ac-RSV-L-CH2Cl (SEQ ID NO:3)

The desired peptide segments are synthesized by one of the following methods: solid phase synthesis using Fmoc/t-Bu chemistry on chlorotrityl resin, solution phase synthesis using Fmoc/t-Bu protocol with the C-terminal orthogonally protected as a methyl, benzyl, or trimethylsilylethyl ester.

Ac-RSV-OH (0.25 mmol) is treated with ethyl chloroformate (0.25 mmol) and Et$_3$N (0.25 mmol) in THF (10 mL) at −15° C. for 20 min. This freshly formed mixed anhydride is added to a stirred solution of hydrochloride salt of Leu-CH$_2$Cl (0.31 mmol) and Et$_3$N (0.31 mmol) in DMF at 0° C. The reaction mixture is stirred at 4° C. overnight. The reaction mixture is diluted with ethyl acetate, washed with 10% citric acid, 5% Na$_2$CO$_3$ and brine, dried over Na$_2$SO$_4$ and concentrated. The crude product is purified by chromatography on silica gel eluted with 2–5% methanol in CH$_2$Cl$_2$ to afford product.

α-Hydroxy Acid Intermediates

α-Hydroxy derivatives of amino acids are useful in preparing certain compounds of the present invention. Preparation of the α-hydroxy derivatives of amino acids can be carried out via a one-carbon homologation of the corresponding α-amino aldehyde. Preparation of Leu-CH(OH)CO$_2$H is illustrative.

To a solution of tris(methylthio)methane (15 mmol) stirred in anhydrous diethyl ether (60 mL) at −78° C. under a dry argon atmosphere is added a solution of n-butyllithium (2.5 M in hexane, 15 mmol) dropwise over a period of 10 min. The resulting solution is stirred for 45 min; then a solution of the Boc-Leu-H (3 mmol) in diethyl ether (5 mL) is slowly added. The solution is stirred for 1.5 h; then a saturated aqueous solution of ammonium chloride solution is added, and the resulting mixture is allowed to warm to room temperature. The mixture is extracted with ethyl acetate (3×100 mL), and the combined extracts are extracted with water and brine and then dried over anhydrous sodium sulfate and filtered. Concentration of the filtrate gives the crude product which is further purified by flash chromatography with gradient solvent system (30–40% ethyl acetate/hexane)to yield products as a diasteromeric mixture. This mixture is then treated with HgCl$_2$ and HgO in methanol at room temperature until the complete consumption of starting materials. The reaction mixture is diluted with ethyl acetate, washed with 0.5 HCl and brine. The organic layer is dried over MgSO$_4$, filtered and concentrated. The crude product is further purified by flash chromatography with a gradient solvent system (1:1 ethyl acetate/hexane)to yield products as a diasteromeric mixture.

Intermediate A: Leu-CH(OH)C(O)NHCH$_2$Ph

To a solution of α-hydroxy acid (1 mmol, see above), HOBT (1.2 mmol), and EDC (1.2 mmol) in THF is added benzylamine (1.2 mmol) followed by diisopropylethylamine (1.5 mmol). The reaction mixture is stirred at room temperature overnight and diluted with 5% citric acid. The organic layer is separated and the aqueous phase extracted three times with AcOEt. The combined extracts are washed with a saturated solution of NaHCO$_3$ and brine, dried over Na$_2$SO$_4$, and filtered. After concentration, the crude product is purified by chromatography.

Intermediate B: Leu-CH(OH)-(1,3-benzothiazol)-2-yl

To a solution of benzothiazole (15 mmol) stirred in anhydrous diethyl ether (60 mL) at −78° C. under a dry argon atmosphere is added a solution of n-butyllithium (2.5 M in hexane, 15 mmol) dropwise over a period of 10 min. The resulting solution is stirred for 45 min; then a solution of the Boc-Leu-H (3 mmol) in diethyl ether (5 mL) is slowly added. The solution is stirred for 1.5 h; then saturated aqueous solution of ammonium chloride solution is added, and the solution is allowed to warm to room temperature. The mixture is extracted with ethyl acetate (3×100 mL), and the combined extracts are washed with water and brine, dried over anhydrous sodium sulfate and filtered. Concentration of the filtrate gives the crude product which is further purified by flash chromatography with gradient elution (30–40% ethyl acetate/hexane) to provide the product as a diasteromeric mixture.

The alcohol compound B (0.5 mmol) is dissolved in CH$_2$Cl$_2$ (5 mL), and Dess-Martin periodane (1 mmol) is added. The mixture is stirred at room temperature for 6 h and then diluted with ethyl acetate and stirred vigorously with 10% aqueous sodium thiosulfate for 10 min. The organic solution is separated, extracted with saturated aqueous sodium bicarbonate, water, and then dried over anhydrous sodium sulfate and filtered. Concentration of the filtrate gives the ketone product.

This crude ketone is dissolved in 95% aqueous trifluoroacetic acid and thioanisole (5%) is added. The resulting solution is stirred at room temperature for 3h to remove all the side chain protecting groups. The thick solution is triturated with diethyl ether and centrifuged. The solution is removed and the solid remaining is triturated and collected as above two more times. The resulting solid is then further purified by reverse phase HPLC.

B. Biological Evaluation of the Compounds

The compounds provided herein can be evaluated for their ability to modulate SREBP processing using an assay to measure the catalytic activity of S1P. The activity measured is typically the inhibition of S1P induced cleavage of a fluorogenic substrate or an HPLC assay to detect S1P induced cleavage of selected peptides in the presence of the compounds provided herein.

The S1P inhibitory activity of the compounds of the present invention can be measured using standard procedures known to those of skill in the art. Briefly, the compounds are contacted with the S1P protein in the presence of a known substrate under conditions (buffer and temperature) optimized to provide maximal protease activity. By quantifying the rate at which substrate is cleaved by the protease in the absence and presence of inhibitor, $IC_{50}$ (the concentration of inhibitor required to provide a 50% reduction in the rate of substrate cleavage), $K_i$ (thermodynamic inhibition constant for reversible inhibitors) or first-order inhibition rate (rate of inactivation of the protease by irreversible inhibitors) values can be determined for each inhibitor.

A variety of methods can be utilized to readily detect the cleavage of the protease substrate, and the design of each substrate is specific to the type of detection method to be utilized.

1. HPLC Assay

HPLC analysis of S1P protease activity uses a large protein or peptide substrate for S1P. At fixed time intervals, reaction aliquots are quenched and quantitation of the peptide fragments produced in carried out by HPLC analysis. Typical substrates possess an amino acid sequence that is well recognized by S1P (e.g., RKVFRSLKFAESDPIV (SEQ ID NO:82) or HSGSGRSVLSFESGSG (SEQ ID NO:83), where protease cleavage occurs after K8 and L9, respectively).

2. Fluorogenic Peptide Assay

Another assay useful for evaluating compounds of the present invention relies on the detection of a cleavage product having fluorogenic or colorimetric properties. A typical colorimetric substrate is RKVFRSLK-SCH$_2$Ph (SEQ ID NO:84) or HSGSGRSVL-SCH$_2$Ph (SEQ ID NO:85). The benzylthiol released from each of these substrates upon proteolytic cleavage by S1P is easily detected by reaction with 4,4'-dinitrodiphenyl disulfide (releasing a yellow 4-nitrophenylsulfide anion having a UV/vis absorbance at 400 nm). Alternatively, a fluorogenic substrate relies on the generation of, for example, 7-amino-4-methylcoumarin (7-AMC) from the 7-AMC amide derivative of an appropriate substrate sequence (e.g., RKVFRSLK-7AMC (SEQ ID NO:86) or HSGSGRSVL-7AMC (SEQ ID NO:87)). Release of the 7-AMC fragment is readily detectable by its fluorescence (360 nm excitation and 460 nm emission/detection).

Other standard methods for studying protease activity such as, for example, the use of Internal Quench (IQ) substrates or doubly-tagged substrates can also be used and are well-known in the art. Doubly-tagged substrates are those in which one end is tagged for solid phase trapping (with, for example, biotin) and the other end is tagged for detection (with, for example, rhodanine).

II. Pharmaceutical Compositions

In another aspect, the present invention provides pharmaceutical compositions comprising a pharmaceutically acceptable carrier or excipient and either a compound of formula (I) or a pharmaceutically acceptable salt of a compound of formula (I). Compounds provided herein which possess $IC_{50}$'s for SREBP processing activity of about 30 µM or less will be particularly useful in the present compositions. More preferably, the compound will have an $IC_{50}$ of about 1 µM or less. Most preferably the compounds will have an $IC_{50}$ of about 0.01 µM or less.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg according to the particular application and the potency of the active component. The composition can, if desired, also contain other compatible therapeutic agents.

III. Diagnostic and Therapeutic Applications

The compounds and compositions of the present invention are useful in a variety of diagnostic and therapeutic applications. Accordingly, in another aspect, the present invention provides methods of inhibiting S1P in a cell. In this aspect, a cell is contacted with an S1P-inhibiting amount of a compound or composition above. An S1P-inhibiting amount can be readily determined using the assays described briefly above, or alternatively, using the assays in the Examples below. Typically, the amount or concentration of compound required to achieve $IC_{50}$ will be considered an S1P-inhibiting amount.

In another aspect, the present invention provides methods of treating conditions modulated by S1P in a host, by administering to the host an effective amount of a compound or composition provided above. In therapeutic applications, the compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally.

A variety of conditions are modulated, at least in part, by S1P, including hypercholesterolemia or other conditions associated with abnormal cholesterol or lipid homeostasis. The compounds utilized in the pharmaceutical method of the invention are administered at the initial dosage of about 0.001 mg/kg to about 100 mg/kg daily. A daily dose range of about 0.1 mg/kg to about 10 mg/kg is preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

In yet another aspect, the present invention provides methods of modulating the expression of genes regulated by SREBP transcription factors in a host, by administering to the host an effective amount of a compound or composition provided above.

In still another aspect, the present invention provides methods of treating conditions associated with abnormal levels of plasma cholesterol, lipoproteins or triglycerides. In this group of embodiments, a subject in need of such treatment is administered an effective amount of a compound or composition provided above.

In each of the methods provided herein, the preferred compounds and compositions are those that have been described in the previous sections. Typically, the host or subject in each of these methods is human, although other animals can also benefit from the foregoing treatments.

EXAMPLES

The examples provided herein describe methods useful for the isolation of S1P as well as methods useful for evaluation of the present compounds and compositions as inhibitors of S1P or modulators of SREBP processing.

Materials

Serum-free CHO-S-SFM II medium was obtained from Life Technologies; Pefabloc® SC, phenylmethylsulfonyl fluoride (PMSF), (4-amindinophenyl)-methanesulfonyl fluoride (APMSF), leupeptin, and pepstatin from Boehringer Mannheim; N-acetyl-leucinal-leucinal-norleucinal (ALLN) from Calbiochem; and aprotinin and 1,10-phenanthroline from Sigma. Ac-Ser-Gly-Arg-Ser-Val-Leu-MCA (SEQ ID NO:88) and Boc-Arg-Val-Arg-Arg-MCA (SEQ ID NO:89) were purchased from Peptide International, Inc. (Louisville, Ky.) and Peninsula Laboratories, Inc. (Belmont, Calif.), respectively. Peptides Ac-Val-Phe-Arg-Ser-Leu-Lys-MCA (SEQ ID NO:90), Ac-Val-Phe-Ala-Ser-Leu-Lys-MCA (SEQ ID NO:91), Ac-Val-Phe-Arg-Ser-Arg-Arg-MCA (SEQ ID NO:92), Ac-Ser-Gly-Ser-Gly-Arg-Ser-Val-Leu-MCA (SEQ ID NO:93), Ac-Arg-Ser-Leu-Lys-MCA (SEQ ID NO:94), and Ac-Arg-Ser-Val-Leu-MCA (SEQ ID NO:95) were synthesized by Tularik Inc. (South San Francisco) by solution coupling of the appropriate fully deprotected peptide fragment with Lys-MCA, Arg-MCA or Leu-MCA followed by RP-HPLC purification. Peptides $NH_2$-Arg-Lys-Val-Phe-Arg-Ser-Leu-Lys-Phe-Ala-Glu-Ser-Asp-Pro-Ile-Val-COOH (SEQ ID NO:96), $NH_2$-His-Ser-Gly-Ser-Gly-Arg-Ser-Val-Leu-Ser-Phe-Glu-Ser-Gly-Ser-Gly-COOH (SEQ ID NO:97), and $NH_2$-His-Ser-Gly-Ser-Gly-Arg-Ser-Ala-Ala-Ser-Phe-Glu-Ser-Gly-Ser-Gly-COOH (SEQ ID NO:98) were synthesized in the laboratory of Clive Slaughter at The University of Texas, Southwestern Medical Center (Dallas, Tex.). IgG-7D4, a mouse monoclonal antibody directed against the $NH_2$-terminal domain of hamster SREBP-2 (amino acids 32–250), was prepared as previously described (see Yang, et al., *J. Biol. Chem.* 270:12152–12161 (1995)).

Construction of Plasmids pCMV-S1P(1052)-Myc-His encodes an 1102-amino acid fuision protein that contains fill-length S1P. It consists of an initiator methionine, amino acids 2–1052 of hamster S1P (see Sakai, et al., *Mol. Cell* 2:505–514 (1998)), three novel amino acids (GGR) encoded by the sequence of the NotI restriction site, three tandem copies of the 9E10 epitope derived from the human c-Myc protein. (EQKLISEEDLGGEQKLISEEDLGPRFEQKLISEEDL; SEQ ID NO:99), five novel amino acids (DMHTG; SEQ ID NO: 100) encoded by linker sequences, and six consecutive histidines. Expression is driven by the CMV promoter/enchancer. pCMV-S1P(1052)-Myc-His was constructed in three steps, as follows. First, an intermediate plasmid (no. 1) was constructed by ligation of three DNA fragments: 1) a~5.4-kb fragment released from the BamHI and NotI digestion of pcDNA3 (Invitrogen); 2) a~4-kb fragment released from the EcoRI and NotI digestion pCMV-S1P (see Sakai, ibid.); and 3) a~150-bp fragment released from the BamHI and EcoRI digestion of a PCR-amplified product obtained from the pCMV-S1P template using the following primers: 5' primer, 5'-CGGGATCCATGAAGC TCATCAACATCTGGC-3' (SEQ ID NO:101); and 3' primer, 5'-GGAGAATTCCACCTTCAAAGTCAGG-3' (SEQ ID NO:102). Second, an intermediate plasmid (no. 2) was constructed by ligation of the following three fragments: a~5.5-kb fragment released from a BamHI and NotI digestion of pcDNA3. 1/Myc-His(+) B (Invitrogen): 2) a~2.6-kb fragment released from a BamHI and NdeI digestion of intermediate plasmid no. 1; and 3) a~550-bp fragment released from the NdeI and NotI digestion of a PCR-amplified product obtained from the pCMV-S1P template using the following primers: 5' primer, 5-TTCAGTACACATCATATGGCGTGAACCCTC-3' (SEQ ID NO:103); and 3' primer, 5'TAGACTCG AGCG-GCCGCCCACTGACGGGGTCCTTGGTGGGTG GGTCTG-3' (SEQ ID NO: 104). Third, a pair of complementary oligonucleotides (top strand, 5'-GGCCGCGAA CAAAAACTCATCTCAGAAGAGGATCTGGGTGGT GAGCAGAAGTTGATTTCTGAGGAAGACCTGG GCC-3' (SEQ ID NO:105); bottom strand, 5'-CAGGTC TTCCTCAGAAATCAACTTCTGCTCACCACCCAG ATCCTCTTCTGAGATGAGTTTTGTTCGC-3' (SEQ ID NO: 106)) were annealed. These oligonucleotides correspond to two additional copies of the c-Myc 9E10 epitope tag. The annealed oligonucleotides were cloned into the ~8-kb fragment released from the ApaI and NotI digestion of intermediate plasmid no. 2. The plasmid resulting from this ligation is designated pCMV-S1P(1052)-Myc-His.

pCMV-S1P(983)-Myc-His encodes the same fuision protein as does pCMV-S1P(1052)-Myc-His, except that the DNA encoding the last 69 amino acids of S1P (residues 984 to 1052) was deleted so as to remove the membrane anchor and COOH-terminal tail. The strategy for the construction of this plasmid was similar to that for pCMV-S1P(1502)-Myc-His except for the second step in which a ~300-bp fragment was amplified from pCMV-S1P using the following primers: 3'- primer: 5'-TAGACTCGAGCGGCCGCCCTCTTG GTTGTAGCGGCCAGGCATGATCC-3' (SEQ ID NO: 107); and the same 5'-primer as described above.

All of the PCR-amplified fragments and ligation junctions in each step of the above construction were confirmed by DNA sequencing.

Transfection of Cells with Epitope-tagged S1P

On day 0, cholesterol auxotrophic SRD-12B cells were plated at a density of $5 \times 10^5$ cells/100-mm dish in medium B (1:1 mixture of Ham's F12 medium and Dulbecco's modified Eagle medium containing 100 units/mL penicillin and 100 µg/mL streptomycin sulfate) supplemented with 5% fetal calf serum 5 µg/mL cholesterol, 1 mM sodium mevalonate, and 20 µM sodium oleate. On day 1, cells were transfected with 5 µg of either pCMV-S1P(1052)-Myc-His or pCMV-S1P(983)-Myc-His and cultured overnight in medium B supplemented with 5% fetal calf serum. On day 2, the medium was switched to medium B supplemented with 5% fetal calf lipoprotein-deficient serum without cholesterol. The medium was changed every second day until individual colonies were visible on day 11. Stable expression of Myc-S1P permitted the growth of SRD-12B cells in the absence of sterols (see, Rawson, et al., J. Biol. Chem. 273:28261–28269 (1998)). Single cell clones that stably expressed S1P were isolated by limiting dilution and analyzed for S1P expression by immunoblotting with the anti-Myc (9E10 clone) monoclonal antibody. The resulting cell lines expressing S1P(1052)-Myc-His (TR-3109 cells) and S1P(983)-Myc-His (TR-3117 cells) are designated S1P (1052) and S1P(983) cells, respectively.

Purification of S1P

Stock cultures of S1P(983) cells were grown in 850-cm² roller bottles in medium B supplemented with 5% (v/v) newborn calf lipoprotein-deficient serum and 500 µg/mL G418. On day 0, 10 roller bottles of S1P(983) cells were seeded at a density of $~4 \times 10^7$ cells/roller bottles. On day 2, the medium was replaced with 100 mL of serum-free medium CHO-S-SFMII. The medium from each roller bottle was collected daily from day 3 to day 7. The collected medium was pooled, filtered through 0.45-µm cellulose acetate low-protein binding membrane filter units (Corning Costar) and stored at 4° C. for 0 to 4 days. On day 7, the filtered medium was adjusted to pH 8.0 by addition of tris-HCl at a final concentration of 25 mM, and then loaded onto four parallel 5-mL Ni-NTA agarose columns (Qiagen, Inc., Chatsworth, Calif.) equilibrated with 20 mL of buffer B (25 mM tris-HCl at pH 8.0, 10% (v/v) glycerol, 1 mM $CaCl_2$). The chromatography was performed at 4° C. via gravity at ~100 mL/hr. The column was washed with 40 mL of buffer B supplemented with 1M NaCl followed by 20 mL of buffer B without NaCl. Elution was achieved with 15 mL of buffer B containing 250 mM imidazole, pH 8. The eluate was concentrated with a Centriprep 30 filter followed by a Centricon 30 filter (Amicon, Inc.). The concentrated solution was supplemented with an equal volume of 100% glycerol and stored in multiple aliquots at –20° C. without loss of activity for at least 4 months. Ten roller bottles of cells yielded 1 mg protein.

Fluorogenic Peptide Assay for S1P Activity

S1P activity was measured fluorometrically with MCA-conjugated peptidyl substrates. Each reaction was carried out in 0.2 mL of assay buffer (25 mM tris, 25 mM Mes, 25 mM acetic acid, and 1 mM $CaCl_2$ adjusted to pH 8.0 with concentrated NaOH). Reactions contained MCA-peptide (final concentration 100 µM, added in 2 µl DMSO) and 1.5–5 µg of purified S1P(187–983). After incubation for 0.5–5 h at 37° C., each reaction was terminated by addition of 1 mL of ice-cold 5 mM sodium EDTA. The liberated 7-amino-4-methylcoumarin (AMC) was measured with a Perkin-Elmer LS-30 luminescence spectrometer (360 nm excitation, 460 nm emission). A standard curve of fluorescence intensity was generated with different concentrations of AMC (Promega).

Table 1 provides the comparative cleavage of fluorogenic synthetic peptidyl substrates by purified S1P-C(187–983).

TABLE 1

| Comparative cleavage of fluorogenic substrates | | |
|---|---|---|
| SEQ ID NO: | Substrate | Relative Activity |
| 90 | Ac-VFRSLK-MCA | 1.0 |
| 94 | Ac-RSLK-MCA | 0.47 |
| 91 | Ac-VFASLK-MCA | <0.1 |
| 88 | Ac-SGRSVL-MCA | <0.1 |
| 93 | Ac-SGSGRSVL-MCA | <0.1 |
| 95 | Ac-RSVL-MCA | <0.1 |
| 92 | Ac-VFRSRR-MCA | <0.1 |
| 89 | Boc-RVRR-MCA | <0.1 |

When incubated with Ac-VFRSLK-MCA (SEQ ID NO:90), S1P was not significantly inhibited by classic inhibitors of trypsin-like serine proteases, such as PMSF and APMSF. High concentrations of Pefabloc®, which is more water soluble than PMSF did inhibit S1P. The enzyme was also resistant to leupeptin, pepstatin, aprotinin and ALLN. It was partially inhibited by EDTA. Extremely high concentrations of EGTA, 1,10-phenanthroline and dithiothreitol also inhibited S1P.

HPLC Assay for S1P Activity

Each reaction was carried out in a final volume of 40 µl of assay buffer (see above) containing a 16-amino acid synthetic peptide (final concentration 300 μM); and 3 μg purified S1P(187–983). After incubation for 4 h at 37° C., the reaction products were separated by reverse-phase HPLC on a 4.6×250-mm RP300 column using a Waters HPLC system. Chromatography was performed in 0.1% (v/v) trifluoracetic acid at 0.75 mL/min. Elution was achieved with a 50-min gradient of 7–50% (v/v) acetontrile. Peptide masses were measured by matrix-assisted laser desorption/ionization (MALDI) mass spectrometry using a Voyager DE time-of-flight mass spectrometer from Persep- tive Biosystems (Framingham, Mass.) with α-cyano-4-hydroxycinnamic acid (Aldrich Chemical) as the matrix.

Although the foregoing invention has been described in some detail by way of illustration and example for purposes of clarity and understanding, it will be apparent that certain changes and modifications may be practiced within the scope of the appended claims. Additionally, each reference provided herein is incorporated by reference in its entirety to the same extent as if each reference was individually incorporated by reference.

What is claimed is:

1. A compound of the formula:

$$R^1-C(=O)-Aa^1-Aa^2-Aa^3-R^2$$

wherein $R^1$ is a member selected from the group consisting of $(C_1-C_6)$alkyl, aryl$(C_1-C_6)$alkyl, aryl, $(C_1-C_6)$alkylamino, aryl$(C_1-C_6)$alkylamino, $(C_1-C_6)$alkoxy, and aryl$(C_1-C_6)$alkoxy;

$Aa^1$ is an amino acid selected from the group consisting of 3-(amidino)phenylglycine, 4-(amidino)phenylglycine, 3-(amidino)phenylalanine, 4-(amidino)phenylalanine, R and K;

$Aa^2$ is an amino acid selected from the group consisting of S, R and N;

$Aa^3$ is an amino acid selected from the group consisting of M, V and L;

$R^2$ is a radical selected from the group consisting of

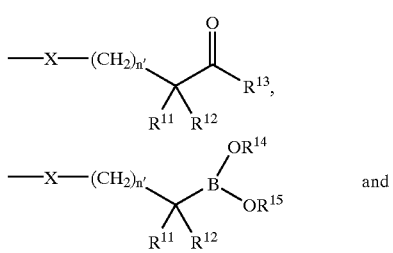

and

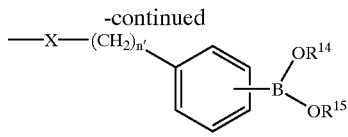

wherein

X is a member selected from the group consisting of O, NH and N—$(C_1-C_4)$alkyl; the subscript n' is an integer of from 0 to 4;

$R^{11}$ and $R^{12}$ are members independently selected from the group consisting of H, $(C_1-C_8)$alkyl, aryl, and aryl$(C_1-C_6)$alkyl; or taken together $R^{11}$ and $R^{12}$ form a five- to seven-membered ring;

$R^{13}$ is a member selected from the group consisting of H, $CF_3$, $CH_2Y$, heteroaryl, $CONHR^{16}$ and $CO_2R^{16}$; wherein Y is a leaving group and $R^{16}$ is selected from the group consisting of H and $(C_1-C_4)$alkyl; and $R^{14}$ and $R^{15}$ are members independently selected from the group consisting of H, $(C_1-C_6)$alkyl, aryl, and aryl$(C_1-C_6)$alkyl.

2. A compound in accordance with claim 1, wherein

X is NH or N$(C_1-C_4)$alkyl; and n' is 0 or 1.

3. A compound in accordance with claim 1, wherein $R^1$ is a member selected from the group consisting of $(C_1-C_3)$alkyl, aryl$(C_1-C_3)$alkyl, $(C_1-C_3)$alkoxy, and aryl$(C_1-C_3)$alkoxy; $R^2$ is selected from the group consisting of:

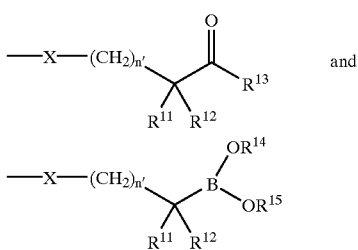

wherein

X is NH;

n' is 0 or 1;

$R^{11}$, $R^{14}$ and $R^{15}$ are each H;

$R^{12}$ is selected from the group consisting of $(C_1-C_4)$alkyl, $(C_2-C_8)$heteroalkyl and aryl$(C_1-C_2)$alkyl; and $R^{13}$ is selected from the group consisting of H, $CH_2Cl$, $CF_3$, heteroaryl, $CO_2R^{16}$ and $CONHR^{16}$.

4. A compound in accordance with claim 1, wherein $R^2$ is a radical of the formula:

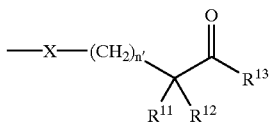

wherein

X is NH, n' is 0, $R^{11}$ is H, $R^{12}$ is a member selected from the group consisting of 2-methyl-1-propyl, methyl, benzyl, 4-amino-1-butyl and 3-guanidino-1-propyl, and $R^{13}$ is a member selected from the group consisting of H, $CH_2Cl$, $CF_3$, CONHEt, $CO_2Et$ and 2-thiazolyl.

5. A compound in accordance with claim 1, said compound being selected from the group consisting of Ac-RSVL-H (SEQ ID NO:2), Ac-RSVL-$CH_2Cl$ (SEQ ID NO:3), Ac-RSVL-$CH_2F$ (SEQ ID NO:4), Ac-RSVL-$CF_3$ (SEQ ID NO:5), Ac-RSVL-CONHEt (SEQ ID NO:6), Ac-RSVL-$CO_2Et$ (SEQ ID NO:7), Ac-RSVL-2-thiazolyl (SEQ ID NO:8), Ac-RSVL-2-benzothiazolyl (SEQ ID NO:9), Ac-RSLL-H (SEQ ID NO:10), Ac-RSLL-$CH_2Cl$ (SEQ ID NO:11), Ac-RSLL-$CH_2F$ (SEQ ID NO:12), Ac-RSLL-$CF_3$ (SEQ ID NO:13), Ac-RSLL-CONHEt (SEQ ID NO:14), Ac-RSLL-$CO_2Et$ (SEQ ID NO:15), Ac-RSLL-2-benzothiazolyl (SEQ ID NO:16), Ac-RSLL-2-thiazolyl (SEQ ID NO:17), Ac-RSLK-H (SEQ ID NO:18), Ac-RSLK-$CH_2Cl$ (SEQ ID NO:19), Ac-RSLK-$CH_2F$ (SEQ ID NO:20), Ac-RSLK-$CF_3$ (SEQ ID NO:21), Ac-RSLK-CONHEt (SEQ ID NO:22), Ac-RSLK-$CO_2Et$ (SEQ ID NO:23), Ac-RSLK-2-thiazolyl (SEQ ID NO:24), Ac-RSLK-2-benzothiazolyl (SEQ ID NO:25), Ac-KSVL-H (SEQ ID NO:26), Ac-KSVL-$CH_2Cl$ (SEQ ID NO:27), Ac-KSVL-$CH_2F$ (SEQ ID NO:28), Ac-KSVL-$CF_3$ (SEQ ID NO:29), Ac-KSVL-CONHEt (SEQ ID NO:30), Ac-KSVL-$CO_2Et$ (SEQ ID NO:31), Ac-KSVL-2-benzothiazolyl (SEQ ID NO:32), Ac-KSVL-2-thiazolyl (SEQ ID NO:33), Ac-RSVK-H (SEQ ID NO:34), Ac-RSVK-$CH_2F$ (SEQ ID NO:35), Ac-RSVK-$CH_2Cl$ (SEQ ID NO:36), Ac-RSVK-$CF_3$ (SEQ ID NO:37), Ac-RSVK-CONHEt (SEQ ID NO:38), Ac-RSVK-$CO_2Et$ (SEQ ID NO:39), Ac-RSVK-2-benzothiazolyl (SEQ ID NO:40) and Ac-RSVK-2-thiazolyl (SEQ ID NO:41).

6. A compound in accordance with claim 1, said compound being selected from the group consisting of Cbz-RSVL-H (SEQ ID NO:42), Cbz-RSVL-$CH_2F$ (SEQ ID NO:43), Cbz-RSVL-$CH_2Cl$ (SEQ ID NO:44), Cbz-RSVL-$CF_3$ (SEQ ID NO:45), Cbz-RSVL-CONHEt (SEQ ID NO:46), Cbz-RSVL-$CO_2Et$ (SEQ ID NO:47), Cbz-RSVL-2-thiazolyl (SEQ ID NO:48), Cbz-RSVL-2-benzothiazolyl (SEQ ID NO:49), Cbz-RSLL-H (SEQ ID NO:50), Cbz-RSLL-$CH_2F$ (SEQ ID NO:51), Cbz-RSLL-$CH_2Cl$ (SEQ ID NO:52), Cbz-RSLL-$CF_3$ (SEQ ID NO:53), Cbz-RSLL-CONHEt (SEQ ID NO:54), Cbz-RSLL-$CO_2Et$(SEQ ID NO:55), Cbz-RSLL-2-thiazolyl (SEQ ID NO:56), Cbz-RSLL-2-benzothiazolyl (SEQ ID NO:57), Cbz-RSLK-H (SEQ ID NO:58), Cbz-RSLK-$CH_2F$ (SEQ ID NO:59), Cbz-RSLK-$CH_2Cl$ (SEQ ID NO:60), Cbz-RSLK-$CF_3$ (SEQ ID NO:61), Cbz-RSLK-CONHEt (SEQ IDNO:62), Cbz-RSLK-$CO_2Et$ (SEQ ID NO:64), Cbz-RSLK-2-thiazolyl (SEQ ID NO:65), Cbz-RSLK-2-benzothiazolyl (SEQ ID NO:66), Cbz-KSVL-H (SEQ ID NO:67), Cbz-KSVL-$CH_2F$ (SEQ ID NO:68), Cbz-KSVL-$CH_2Cl$ (SEQ ID NO:69), Cbz-KSVL-$CF_3$ (SEQ ID NO:69), Cbz-KSVL-CONHEt (SEQ ID NO:70), Cbz-KSVL-$CO_2Et$ (SEQ ID NO:71), Cbz-KSVL-2-thiazolyl (SEQ ID NO:72), Cbz-KSVL-2-benzothiazolyl (SEQ ID NO:73), Cbz-RSVK-H (SEQ ID NO:74), Cbz-RSVK-$CH_2F$ (SEQ ID NO:75), Cbz-RSVK-$CH_2Cl$ (SEQ ID NO:76), Cbz-RSVK-$CF_3$ (SEQ ID NO:77), Cbz-RSVK-CONHEt (SEQ ID NO:78), Cbz-RSVK-$CO_2Et$ (SEQ ID NO:79), Cbz-RSVK-2-thiazolyl (SEQ ID NO:80) and Cbz-RSVK-2-benzothiazolyl (SEQ ID NO:81).

7. A pharmaceutical composition comprising a pharmaceutically acceptable excipient and a compound of the formula:

$$R^1-C(=O)-Aa^1-Aa^2-Aa^3-R^2$$

wherein $R^1$ is a member selected from the group consisting of $(C_1-C_6)$alkyl, aryl$(C_1-C_6)$alkyl, aryl, $(C_1-C_6)$alkylamino, aryl$(C_1-C_6)$alkylamino, $(C_1-C_6)$alkoxy, and aryl$(C_1-C_6)$alkoxy;

$Aa^1$ is an amino acid selected from the group consisting of 3-(amidino)phenylglycine, 4-(amidino)phenylglycine, 3-(amidino)phenylalanine, 4-(amidino)phenylalanine, R and K;

$Aa^2$ is an amino acid selected from the group consisting of S, R and N;

$Aa^3$ is an amino acid selected from the group consisting of M, V and L;

$R^2$ is a radical selected from the group consisting of

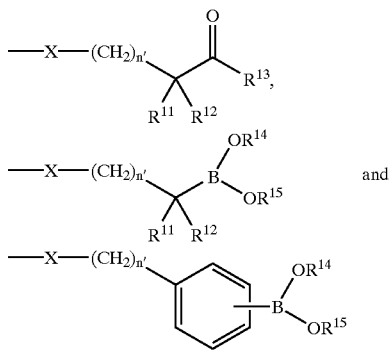

wherein

X is a member selected from the group consisting of O, NH and N—$(C_1-C_4)$alkyl;

the subscript n' is an integer of from 0 to 4;

$R^{11}$ and $R^{12}$ are members independently selected from the group consisting of H, $(C_1-C_8)$alkyl, aryl, and aryl $(C_1-C_6)$alkyl; or taken together $R^{11}$ and $R^{12}$ form a five- to seven-membered ring;

$R^{13}$ is a member selected from the group consisting of H, $CF_3$, $CH_2Y$, heteroaryl, $CONHR^{16}$ and $CO_2R^{16}$; wherein Y is a leaving group and $R^{16}$ is selected from the group consisting of H and $(C_1-C_4)$alkyl; and $R^{14}$ and $R^{15}$ are members independently selected from the group consisting of H, $(C_1-C_6)$alkyl, aryl, and aryl $(C_1-C_6)$alkyl.

8. A pharmaceutical composition in accordance with claim 7,
wherein
X is NH or $N(C_1-C_4)$alkyl; and
n' is 0 or 1.

9. A pharmaceutical composition in accordance with claim 7, wherein $R^1$ is a member selected from the group consisting of $(C_1-C_3)$alkyl, aryl$(C_1-C_3)$alkyl, $(C_1-C_3)$alkoxy, and aryl$(C_1-C_3)$alkoxy; $R^2$ is selected from the group consisting of:

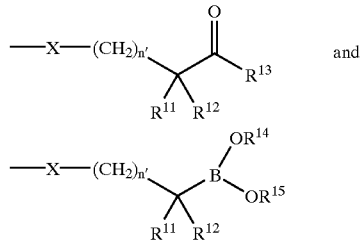

wherein
X is NH;
n' is 0 or 1;
$R^{11}$, $R^{14}$ and $R^{15}$ are each H;
$R^{12}$ is selected from the group consisting of $(C_1-C_4)$alkyl, $(C_2-C_8)$heteroalkyl and aryl$(C_1-C_2)$alkyl; and
$R^{13}$ is selected from the group consisting of H, $CH_2Cl$, $CF_3$, heteroaryl, $CO_2R^{16}$ and $CONHR^{16}$.

10. A pharmaceutical composition in accordance with claim 7, wherein $R^2$ is a radical of the formula:

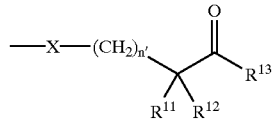

wherein
X is NH, n' is 0, $R^{11}$ is H, $R^{12}$ is a member selected from the group consisting of 2-methyl-1-propyl, methyl, benzyl, 4-amino-1-butyl and 3-guanidino-1-propyl, and $R^{13}$ is a member selected from the group consisting of H, $CH_2Cl$, $CF_3$, CONHEt, $CO_2Et$ and 2-thiazolyl.

11. A pharmaceutical composition in accordance with claim 7, said compound being selected from the group consisting of Ac-RSVL-H (SEQ ID NO:2), Ac-RSVL-CH$_2$Cl (SEQ ID NO:3), Ac-RSVL-CH$_2$F (SEQ ID NO:4), Ac-RSVL-CF$_3$ (SEQ ID NO:5), Ac-RSVL-CONHEt (SEQ ID NO:6), Ac-RSVL-CO$_2$Et (SEQ ID NO:7), Ac-RSVL-2-thiazolyl (SEQ ID NO:8), Ac-RSVL-2-benzothiazolyl (SEQ ID NO:9), Ac-RSLL-H (SEQ ID NO:10), Ac-RSLL-CH$_2$Cl (SEQ ID NO:11), Ac-RSLL-CH$_2$F (SEQ ID NO:12), Ac-RSLL-CF$_3$ (SEQ ID NO:13), Ac-RSLL-CONHEt (SEQ ID NO:14), Ac-RSLL-CO$_2$Et (SEQ IDNO:15), Ac-RSLL-2-benzothiazolyl (SEQ ID NO:16), Ac-RSLL-2-thiazolyl (SEQ ID NO:17), Ac-RSLK-H (SEQ ID NO:18), Ac-RSLK-CH$_2$Cl (SEQ ID NO:19), Ac-RSLK-CH$_2$F (SEQ ID NO:20), Ac-RSLK-CF$_3$ (SEQ ID NO:21), Ac-RSLK-CONHEt (SEQ ID NO:22), Ac-RSLK-CO$_2$Et (SEQ ID NO:23), Ac-RSLK-2-thiazolyl (SEQ ID NO:24), Ac-RSLK-2-benzothiazolyl (SEQ ID NO:25), Ac-KSVL-H (SEQ ID NO:26), Ac-KSVL-CH$_2$Cl (SEQ ID NO:27), Ac-KSVL-CH$_2$F (SEQ ID NO:28), Ac-KSVL-CF$_3$ (SEQ ID NO:29), Ac-KSVL-CONHEt (SEQ ID NO:30), Ac-KSVL-CO$_2$Et (SEQ ID NO:31), Ac-KSVL-2-benzothiazolyl (SEQ ID NO:32), Ac-KSVL-2-thiazolyl (SEQ ID NO:33), Ac-RSVK-H (SEQ ID NO:34), Ac-RSVK-CH$_2$F (SEQ ID NO:35), Ac-RSVK-CH$_2$Cl (SEQ ID NO:36), Ac-RSVK-CF$_3$ (SEQ ID NO:37), Ac-RSVK-CONHEt (SEQ ID NO:38), Ac-RSVK-CO$_2$Et (SEQ ID NO:39), Ac-RSVK-2-benzothiazolyl (SEQ ID NO:40) and Ac-RSVK-2-thiazolyl (SEQ ID NO:41).

12. A pharmaceutical composition in accordance with claim 7, said compound being selected from the group consisting of Cbz-RSVL-H (SEQ ID NO:42), Cbz-RSVL-CH$_2$F (SEQ ID NO:43), Cbz-RSVL-CH$_2$Cl (SEQ ID NO:44), Cbz-RSVL-CF$_3$ (SEQ ID NO:45), Cbz-RSVL-CONHEt (SEQ ID NO:46), Cbz-RSVL-CO$_2$Et (SEQ ID NO:47), Cbz-RSVL-2-thiazolyl (SEQ ID NO:48), Cbz-RSVL-2-benzothiazolyl (SEQ ID NO:49), Cbz-RSLL-H (SEQ ID NO:50), Cbz-RSLL-CH$_2$F (SEQ ID NO:51), Cbz-RSLL-CH$_2$Cl (SEQ ID NO:52), Cbz-RSLL-CF$_3$ (SEQ ID NO:53), Cbz-RSLL-CONHEt (SEQ ID NO:54), Cbz-RSLL-CO$_2$Et (SEQ ID NO:55), Cbz-RSLL-2-thiazolyl (SEQ ID NO:56), Cbz-RSLL-2-benzothiazolyl (SEQ ID NO:57), Cbz-RSLK-H (SEQ ID NO:58), Cbz-RSLK-CH$_2$F (SEQ ID NO:59), Cbz-RSLK-CH$_2$Cl (SEQ ID NO:60), Cbz-RSLK-CF$_3$ (SEQ ID NO:61), Cbz-RSLK-CONHEt (SEQ ID NO:62), Cbz-RSLK-CO$_2$Et (SEQ ID NO:64), Cbz-RSLK-2-thiazolyl (SEQ ID NO:65), Cbz-RSLK-2-benzothiazolyl (SEQ ID NO:66), Cbz-KSVL-H (SEQ ID NO:67), Cbz-KSVL-CH$_2$F (SEQ ID NO:68), Cbz-KSVL-CH$_2$Cl (SEQ ID NO:69), Cbz-KSVL-CF$_3$ (SEQ ID NO:69), Cbz-KSVL-CONHEt (SEQ ID NO:70), Cbz-KSVL-CO$_2$Et (SEQ ID NO:71), Cbz-KSVL-2-thiazolyl (SEQ ID NO:72), Cbz-KSVL-2-benzothiazolyl (SEQ ID NO:73), Cbz-RSVK-H (SEQ ID NO:74), Cbz-RSVK-CH$_2$F (SEQ ID NO:75), Cbz-RSVK-CH$_2$Cl (SEQ ID NO:76), Cbz-RSVK-CF$_3$ (SEQ ID NO:77), Cbz-RSVK-CONHEt (SEQ ID NO:78), Cbz-RSVK-CO$_2$Et (SEQ ID NO:79), Cbz-RSVK-2-thiazolyl (SEQ ID NO:80) and Cbz-RSVK-2-benzothiazolyl (SEQ ID NO:81).

* * * * *

UNITED STATES PATENT AND TRADEMARK OFFICE
CERTIFICATE OF CORRECTION

PATENT NO.   : 6,649,593 B1  Page 1 of 1
DATED        : November 18, 2003
INVENTOR(S)  : Juan C. Jaen et al.

It is certified that error appears in the above-identified patent and that said Letters Patent is hereby corrected as shown below:

Column 75,
Line 32, following "n' is" replace "O" with -- 0 --.

Column 77,
Line 51, "n' is" replace "O" with -- 0 --.

Signed and Sealed this

Ninth Day of March, 2004

JON W. DUDAS
*Acting Director of the United States Patent and Trademark Office*

SEQUENCE LISTING

```
<160> NUMBER OF SEQ ID NOS: 107

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:Site-1
      protease (S1P) cleavage sequence

<400> SEQUENCE: 1

Arg Ser Val Leu
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg

<400> SEQUENCE: 2

Xaa Ser Val Leu
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Leu modified by chloromethylketone
      (-CH-2Cl)

<400> SEQUENCE: 3

Xaa Ser Val Xaa
  1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
```

```
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Leu modified by fluoromethylketone
      (-CH-2F)

<400> SEQUENCE: 4

Xaa Ser Val Xaa
  1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Leu modified by trifluoromethylketone
      (-CF-3)

<400> SEQUENCE: 5

Xaa Ser Val Xaa
  1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Leu modified by N-ethyl alpha-ketoamide
      (-CONHEt)

<400> SEQUENCE: 6

Xaa Ser Val Xaa
  1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Leu modified by ethyl ester (-CO-2Et)

<400> SEQUENCE: 7

Xaa Ser Val Xaa
  1

<210> SEQ ID NO 8
<211> LENGTH: 4
<212> TYPE: PRT
<213> ORGANISM: Artificial Sequence
```

```
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = 2-thiazolyl Leu

<400> SEQUENCE: 8

Xaa Ser Val Xaa
  1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = 2-benzothiazolyl Leu

<400> SEQUENCE: 9

Xaa Ser Val Xaa
  1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg

<400> SEQUENCE: 10

Xaa Ser Leu Leu
  1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Leu modified by chloromethylketone
      (-CH-2Cl)

<400> SEQUENCE: 11

Xaa Ser Leu Xaa
  1

<210> SEQ ID NO 12
<211> LENGTH: 4
<212> TYPE: PRT
<213> ORGANISM: Artificial Sequence
<220> FEATURE:
```

```
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Leu modified by fluoromethylketone
      (-CH-2F)

<400> SEQUENCE: 12

Xaa Ser Leu Xaa
 1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Leu modified by trifluoromethylketone
      (-CF-3)

<400> SEQUENCE: 13

Xaa Ser Leu Xaa
 1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Leu modified by N-ethyl alpha-ketoamide
      (-CONHEt)

<400> SEQUENCE: 14

Xaa Ser Leu Xaa
 1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Leu modified by ethyl ester (-CO-2Et)

<400> SEQUENCE: 15

Xaa Ser Leu Xaa
 1

<210> SEQ ID NO 16
```

```
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = 2-benzothiazolyl Leu

<400> SEQUENCE: 16

Xaa Ser Leu Xaa
  1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = 2-thiazolyl Leu

<400> SEQUENCE: 17

Xaa Ser Leu Xaa
  1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg

<400> SEQUENCE: 18

Xaa Ser Leu Lys
  1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Lys modified by chloromethylketone
      (-CH-2Cl)

<400> SEQUENCE: 19

Xaa Ser Leu Xaa
  1

<210> SEQ ID NO 20
<211> LENGTH: 4
```

```
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Lys modified by fluoromethylketone
      (-CH-2F)

<400> SEQUENCE: 20

Xaa Ser Leu Xaa
  1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Lys modified by trifluoromethylketone
      (-CF-3)

<400> SEQUENCE: 21

Xaa Ser Leu Xaa
  1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Lys modified by N-ethyl alpha-ketoamide
      (-CONHEt)

<400> SEQUENCE: 22

Xaa Ser Leu Xaa
  1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Lys modified by ethyl ester (-CO-2Et)

<400> SEQUENCE: 23

Xaa Ser Leu Xaa
  1
```

```
<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = 2-thiazolyl Lys

<400> SEQUENCE: 24

Xaa Ser Leu Xaa
 1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = 2-benzothiazolyl Lys

<400> SEQUENCE: 25

Xaa Ser Leu Xaa
 1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Lys

<400> SEQUENCE: 26

Xaa Ser Val Leu
 1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Lys
<221> NAME/KEY: MOD_RES
<222> LOCATION: (4)
<223> OTHER INFORMATION: Xaa = Leu modified by chloromethylketone
      (-CH-2Cl)

<400> SEQUENCE: 27

Xaa Ser Val Xaa
 1
```

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Lys
<221> NAME/KEY: MOD_RES
<222> LOCATION: (4)
<223> OTHER INFORMATION: Xaa = Leu modified by fluoromethylketone
      (-CH-2F)

<400> SEQUENCE: 28

Xaa Ser Val Xaa
 1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Lys
<221> NAME/KEY: MOD_RES
<222> LOCATION: (4)
<223> OTHER INFORMATION: Xaa = Leu modified by trifluoromethylketone
      (-CF-3)

<400> SEQUENCE: 29

Xaa Ser Val Xaa
 1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Lys
<221> NAME/KEY: MOD_RES
<222> LOCATION: (4)
<223> OTHER INFORMATION: Xaa = Leu modified by N-ethyl alpha-ketoamide
      (-CONHEt)

<400> SEQUENCE: 30

Xaa Ser Val Xaa
 1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Lys
<221> NAME/KEY: MOD_RES
<222> LOCATION: (4)
<223> OTHER INFORMATION: Xaa = Leu modified by ethyl ester (-CO-2Et)

<400> SEQUENCE: 31

Xaa Ser Val Xaa
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Lys
<221> NAME/KEY: MOD_RES
<222> LOCATION: (4)
<223> OTHER INFORMATION: Xaa = 2-benzothiazolyl Leu

<400> SEQUENCE: 32

Xaa Ser Val Xaa
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Lys
<221> NAME/KEY: MOD_RES
<222> LOCATION: (4)
<223> OTHER INFORMATION: Xaa = 2-thiazolyl Leu

<400> SEQUENCE: 33

Xaa Ser Val Xaa
1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg

<400> SEQUENCE: 34

Xaa Ser Val Lys
1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Lys modified by fluoromethylketone
      (-CH-2F)

<400> SEQUENCE: 35

```
Xaa Ser Val Xaa
  1

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Lys modified by chloromethylketone
      (-CH-2Cl)

<400> SEQUENCE: 36

Xaa Ser Val Xaa
  1

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Lys modified by trifluoromethylketone
      (-CF-3)

<400> SEQUENCE: 37

Xaa Ser Val Xaa
  1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Lys modified by N-ethyl alpha-ketoamide
      (-CONHEt)

<400> SEQUENCE: 38

Xaa Ser Val Xaa
  1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
```

```
<223> OTHER INFORMATION: Xaa = Lys modified by ethyl ester (-CO-2Et)

<400> SEQUENCE: 39

Xaa Ser Val Xaa
  1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = 2-benzothiazolyl Lys

<400> SEQUENCE: 40

Xaa Ser Val Xaa
  1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = 2-thiazolyl Lys

<400> SEQUENCE: 41

Xaa Ser Val Xaa
  1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Leu modified by fluoromethylketone
      (-CH-2F)

<400> SEQUENCE: 42

Xaa Ser Val Leu
  1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
```

```
<221> NAME/KEY: MOD_RES
<222> LOCATION: (4)
<223> OTHER INFORMATION: Xaa = Leu modified by fluoromethylketone
      (-CH-2F)

<400> SEQUENCE: 43

Xaa Ser Val Xaa
  1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Leu modified by chloromethylketone
      (-CH-2Cl)

<400> SEQUENCE: 44

Xaa Ser Val Xaa
  1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Leu modified by trifluoromethylketone
      (-CF-3)

<400> SEQUENCE: 45

Xaa Ser Val Xaa
  1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Leu modified by N-ethyl alpha-ketoamide
      (-CONHEt)

<400> SEQUENCE: 46

Xaa Ser Val Xaa
  1

<210> SEQ ID NO 47
<211> LENGTH: 4
<212> TYPE: PRT
<213> ORGANISM: Artificial Sequence
<220> FEATURE:
```

```
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Leu modified by ethyl ester (-CO-2Et)

<400> SEQUENCE: 47

Xaa Ser Val Xaa
  1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = 2-thiazolyl Leu

<400> SEQUENCE: 48

Xaa Ser Val Xaa
  1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = 2-benzothiazolyl Leu

<400> SEQUENCE: 49

Xaa Ser Val Xaa
  1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg

<400> SEQUENCE: 50

Xaa Ser Leu Leu
  1

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
```

```
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Leu modified by fluoromethylketone
      (-CH-2F)

<400> SEQUENCE: 51

Xaa Ser Leu Xaa
  1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Leu modified by chloromethylketone
      (-CH-2Cl)

<400> SEQUENCE: 52

Xaa Ser Leu Xaa
  1

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Leu modified by trifluoromethylketone
      (-CF-3)

<400> SEQUENCE: 53

Xaa Ser Leu Xaa
  1

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Leu modified by N-ethyl alpha-ketoamide
      (-CONHEt)

<400> SEQUENCE: 54

Xaa Ser Leu Xaa
  1

<210> SEQ ID NO 55
<211> LENGTH: 4
```

```
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Leu modified by ethyl ester (-CO-2Et)

<400> SEQUENCE: 55

Xaa Ser Leu Xaa
  1

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = 2-thiazolyl Leu

<400> SEQUENCE: 56

Xaa Ser Leu Xaa
  1

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = 2-benzothiazolyl Leu

<400> SEQUENCE: 57

Xaa Ser Leu Xaa
  1

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg

<400> SEQUENCE: 58

Xaa Ser Leu Lys
  1

<210> SEQ ID NO 59
<211> LENGTH: 4
<212> TYPE: PRT
<213> ORGANISM: Artificial Sequence
```

```
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Lys modified by fluoromethylketone
      (-CH-2F)

<400> SEQUENCE: 59

Xaa Ser Leu Xaa
 1

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Lys modified by chloromethylketone
      (-CH-2Cl)

<400> SEQUENCE: 60

Xaa Ser Leu Xaa
 1

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Lys modified by trifluoromethylketone
      (-CF-3)

<400> SEQUENCE: 61

Xaa Ser Leu Xaa
 1

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Lys modified by N-ethyl alpha-ketoamide
      (-CONHEt)

<400> SEQUENCE: 62

Xaa Ser Leu Xaa
 1
```

```
<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Lys modified by ethyl ester (-CO-2Et)

<400> SEQUENCE: 63

Xaa Ser Leu Xaa
  1

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = 2-thiazolyl Lys

<400> SEQUENCE: 64

Xaa Ser Leu Xaa
  1

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = 2-benzothiazolyl Lys

<400> SEQUENCE: 65

Xaa Ser Leu Xaa
  1

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Lys

<400> SEQUENCE: 66

Xaa Ser Val Leu
  1

<210> SEQ ID NO 67
```

```
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Lys
<221> NAME/KEY: MOD_RES
<222> LOCATION: (4)
<223> OTHER INFORMATION: Xaa = Leu modified by fluoromethylketone
      (-CH-2F)

<400> SEQUENCE: 67

Xaa Ser Val Xaa
  1

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Lys
<221> NAME/KEY: MOD_RES
<222> LOCATION: (4)
<223> OTHER INFORMATION: Xaa = Leu modified by chloromethylketone
      (-CH-2Cl)

<400> SEQUENCE: 68

Xaa Ser Val Xaa
  1

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Lys
<221> NAME/KEY: MOD_RES
<222> LOCATION: (4)
<223> OTHER INFORMATION: Xaa = Leu modified by trifluoromethylketone
      (-CF-3)

<400> SEQUENCE: 69

Xaa Ser Val Xaa
  1

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Lys
<221> NAME/KEY: MOD_RES
<222> LOCATION: (4)
<223> OTHER INFORMATION: Xaa = Leu modified by N-ethyl alpha-ketoamide
      (-CONHEt)

<400> SEQUENCE: 70
```

Xaa Ser Val Xaa
1

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Lys
<221> NAME/KEY: MOD_RES
<222> LOCATION: (4)
<223> OTHER INFORMATION: Xaa = Leu modified by ethyl ester (-CO-2Et)

<400> SEQUENCE: 71

Xaa Ser Val Xaa
1

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Lys
<221> NAME/KEY: MOD_RES
<222> LOCATION: (4)
<223> OTHER INFORMATION: Xaa = 2-thiazolyl Leu

<400> SEQUENCE: 72

Xaa Ser Val Xaa
1

<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Lys
<221> NAME/KEY: MOD_RES
<222> LOCATION: (4)
<223> OTHER INFORMATION: Xaa = 2-benzothiazolyl Leu

<400> SEQUENCE: 73

Xaa Ser Val Xaa
1

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg

<400> SEQUENCE: 74

Xaa Ser Val Lys
1

```
<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Lys modified by fluoromethylketone
      (-CH-2F)

<400> SEQUENCE: 75

Xaa Ser Val Xaa
  1

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Lys modified by chloromethylketone
      (-CH-2Cl)

<400> SEQUENCE: 76

Xaa Ser Val Xaa
  1

<210> SEQ ID NO 77
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Lys modified by trifluoromethylketone
      (-CF-3)

<400> SEQUENCE: 77

Xaa Ser Val Xaa
  1

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Lys modified by N-ethyl alpha-ketoamide
      (-CONHEt)
```

```
<400> SEQUENCE: 78

Xaa Ser Val Xaa
  1

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = Lys modified by ethyl ester (-CO-2Et)

<400> SEQUENCE: 79

Xaa Ser Val Xaa
  1

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = 2-thiazolyl Lys

<400> SEQUENCE: 80

Xaa Ser Val Xaa
  1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence:tetrapeptide
      Site-1 protease (S1P) inhibitor
<221> NAME/KEY: MOD_RES
<222> LOCATION: (1)
<223> OTHER INFORMATION: Xaa = benzyloxycarbonyl (Cbz) Arg
<221> NAME/KEY: MOD_RES
<222> LOCATION: (4)
<223> OTHER INFORMATION: Xaa = 2-benzothiazolyl Lys

<400> SEQUENCE: 81

Xaa Ser Val Xaa
  1

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence:typical
      Site-1 protease (S1P) peptide cleavage substrate

<400> SEQUENCE: 82

Arg Lys Val Phe Arg Ser Leu Lys Phe Ala Glu Ser Asp Pro Ile Val
  1               5                  10                  15
```

```
<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence:typical
      Site-1 protease (S1P) peptide cleavage substrate

<400> SEQUENCE: 83

His Ser Gly Ser Gly Arg Ser Val Leu Ser Phe Glu Ser Gly Ser Gly
  1               5                  10                  15

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence:typical
      Site-1 protease (S1P) colorimetric substrate
<221> NAME/KEY: MOD_RES
<222> LOCATION: (8)
<223> OTHER INFORMATION: Xaa = Lys modified by benzylthiol (-SCH-2Ph)

<400> SEQUENCE: 84

Arg Lys Val Phe Arg Ser Leu Xaa
  1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence:typical
      Site-1 protease (S1P) colorimetric substrate
<221> NAME/KEY: MOD_RES
<222> LOCATION: (9)
<223> OTHER INFORMATION: Xaa = Leu modified by benzylthiol (-SCH-2Ph)

<400> SEQUENCE: 85

His Ser Gly Ser Gly Arg Ser Val Xaa
  1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence:Site-1
      protease (S1P) fluorogenic substrate
<221> NAME/KEY: MOD_RES
<222> LOCATION: (8)
<223> OTHER INFORMATION: Xaa = Lys modified by 7-amino-4-methylcoumarin
      (7-AMC) amide

<400> SEQUENCE: 86

Arg Lys Val Phe Arg Ser Leu Xaa
  1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence:Site-1
      protease (S1P) fluorogenic substrate
<221> NAME/KEY: MOD_RES
<222> LOCATION: (9)
<223> OTHER INFORMATION: Xaa = Leu modified by 7-amino-4-methylcoumarin
      (7-AMC) amide
```

```
<400> SEQUENCE: 87

His Ser Gly Ser Gly Arg Ser Val Xaa
  1               5

<210> SEQ ID NO 88
<211> LENGTH: 6
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa = N-acetyl Ser
<223> OTHER INFORMATION: Description of Artificial Sequence:synthetic
      MCA-conjugated Site-1 peptidase (S1P) fluorogenic
      peptidyl substrates
<221> NAME/KEY: MOD_RES
<222> LOCATION: (1)
<223> OTHER INFORMATION: Xaa = N-acetyl Ser
<221> NAME/KEY: MOD_RES
<222> LOCATION: (6)
<223> OTHER INFORMATION: Xaa = Leu modified by 4-methyl-coumaryl-7-amide
      (MCA)

<400> SEQUENCE: 88

Xaa Gly Arg Ser Val Xaa
  1               5

<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence:synthetic
      MCA-conjugated Site-1 peptidase (S1P) fluorogenic
      peptidyl substrates
<221> NAME/KEY: MOD_RES
<222> LOCATION: (1)
<223> OTHER INFORMATION: Xaa = t-butyloxycabonyl (Boc) Arg
<221> NAME/KEY: MOD_RES
<222> LOCATION: (4)
<223> OTHER INFORMATION: Xaa = Arg modified by 4-methyl-coumaryl-7-amide
      (MCA)

<400> SEQUENCE: 89

Xaa Val Arg Xaa
  1

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence:synthetic
      MCA-conjugated Site-1 peptidase (S1P) fluorogenic
      peptidyl substrates
<221> NAME/KEY: MOD_RES
<222> LOCATION: (1)
<223> OTHER INFORMATION: Xaa = N-acetyl Val
<221> NAME/KEY: MOD_RES
<222> LOCATION: (6)
<223> OTHER INFORMATION: Xaa = Lys modified by 4-methyl-coumaryl-7-amide
      (MCA)

<400> SEQUENCE: 90

Xaa Phe Arg Ser Leu Xaa
  1               5

<210> SEQ ID NO 91
<211> LENGTH: 6
<212> TYPE: PRT
```

```
<213> ORGANISM: Artificial Sequence
<220> FEATURE:
<223> OTHER INFORMATION: Description of Artificial Sequence:synthetic
      MCA-conjugated Site-1 peptidase (S1P) fluorogenic
      peptidyl substrates
<221> NAME/KEY: MOD_RES
<222> LOCATION: (1)
<223> OTHER INFORMATION: Xaa = N-acetyl Val
<221> NAME/KEY: MOD_RES
<222> LOCATION: (6)
<223> OTHER INFORMATION: Xaa = Lys modified by 4-methyl-coumaryl-7-amide
      (MCA)

<400> SEQUENCE: 91

Xaa Phe Ala Ser Leu Xaa
 1               5

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence:synthetic
      MCA-conjugated Site-1 peptidase (S1P) fluorogenic
      peptidyl substrates
<221> NAME/KEY: MOD_RES
<222> LOCATION: (1)
<223> OTHER INFORMATION: Xaa = N-acetyl Val
<221> NAME/KEY: MOD_RES
<222> LOCATION: (6)
<223> OTHER INFORMATION: Xaa = Arg modified by 4-methyl-coumaryl-7-amide
      (MCA)

<400> SEQUENCE: 92

Xaa Phe Arg Ser Arg Xaa
 1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence:synthetic
      MCA-conjugated Site-1 peptidase (S1P) fluorogenic
      peptidyl substrates
<221> NAME/KEY: MOD_RES
<222> LOCATION: (1)
<223> OTHER INFORMATION: Xaa = N-acetyl Ser
<221> NAME/KEY: MOD_RES
<222> LOCATION: (8)
<223> OTHER INFORMATION: Xaa = Leu modified by 4-methyl-coumaryl-7-amide
      (MCA)

<400> SEQUENCE: 93

Xaa Gly Ser Gly Arg Ser Val Xaa
 1               5

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence:synthetic
      MCA-conjugated Site-1 peptidase (S1P) fluorogenic
      peptidyl substrates
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Lys modified by 4-methyl-coumaryl-7-amide
      (MCA)
```

```
<400> SEQUENCE: 94

Xaa Ser Leu Xaa
 1

<210> SEQ ID NO 95
<211> LENGTH: 4
<212> TYPE: PRT
<213> ORGANISM: Artificial Sequence
<220> FEATURE:
<223> OTHER INFORMATION: Description of Artificial Sequence:synthetic
      MCA-conjugated Site-1 peptidase (S1P) fluorogenic
      peptidyl substrates
<221> NAME/KEY: MOD_RES
<222> LOCATION: (1)
<223> OTHER INFORMATION: Xaa = N-acetyl Arg
<221> NAME/KEY: MOD_RES
<222> LOCATION: (4)
<223> OTHER INFORMATION: Xaa = Leu modified by 4-methyl-coumaryl-7-amide
      (MCA)

<400> SEQUENCE: 95

Xaa Ser Val Xaa
 1

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence:synthesized
      peptide

<400> SEQUENCE: 96

Arg Lys Val Phe Arg Ser Leu Lys Phe Ala Glu Ser Asp Pro Ile Val
 1               5                  10                  15

<210> SEQ ID NO 97
<211> LENGTH: 16
<212> TYPE: PRT
<213> ORGANISM: Artificial Sequence
<220> FEATURE:
<223> OTHER INFORMATION: Description of Artificial Sequence:synthesized
      peptide

<400> SEQUENCE: 97

His Ser Gly Ser Gly Arg Ser Val Leu Ser Phe Glu Ser Gly Ser Gly
 1               5                  10                  15

<210> SEQ ID NO 98
<211> LENGTH: 16
<212> TYPE: PRT
<213> ORGANISM: Artificial Sequence
<220> FEATURE:
<223> OTHER INFORMATION: Description of Artificial Sequence:synthesized
      peptide

<400> SEQUENCE: 98

His Ser Gly Ser Gly Arg Ser Ala Ala Ser Phe Glu Ser Gly Ser Gly
 1               5                  10                  15

<210> SEQ ID NO 99
<211> LENGTH: 36
<212> TYPE: PRT
<213> ORGANISM: Artificial Sequence
<220> FEATURE:
<223> OTHER INFORMATION: Description of Artificial Sequence:three tandem
      copies of the 9E10 epitope derived from human
      c-Myc protein
```

-continued

```
<400> SEQUENCE: 99

Glu Gln Lys Leu Ile Ser Glu Glu Asp Leu Gly Gly Glu Gln Lys Leu
 1               5                  10                  15

Ile Ser Glu Glu Asp Leu Gly Pro Arg Phe Glu Gln Lys Leu Ile Ser
                20                  25                  30

Glu Glu Asp Leu
         35

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence:five novel
      amino acids encoded by linker sequences

<400> SEQUENCE: 100

Asp Met His Thr Gly
 1               5

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence:5' primer

<400> SEQUENCE: 101
cgggatccat gaagctcatc aacatctggc                                           30

<210> SEQ ID NO 102
<211> LENGTH: 25
<212> TYPE: DNA
<213> ORGANISM: Artificial Sequence
<220> FEATURE:
<223> OTHER INFORMATION: Description of Artificial Sequence:3' primer

<400> SEQUENCE: 102
ggagaattcc accttcaaag tcagg                                                25

<210> SEQ ID NO 103
<211> LENGTH: 30
<212> TYPE: DNA
<213> ORGANISM: Artificial Sequence
<220> FEATURE:
<223> OTHER INFORMATION: Description of Artificial Sequence:5' primer

<400> SEQUENCE: 103
ttcagtacac atcatatggc gtgaaccctc                                           30

<210> SEQ ID NO 104
<211> LENGTH: 48
<212> TYPE: DNA
<213> ORGANISM: Artificial Sequence
<220> FEATURE:
<223> OTHER INFORMATION: Description of Artificial Sequence:3' primer

<400> SEQUENCE: 104
tagactcgag cggccgccca ctgacggggt ccttggtggg tgggtctg                       48

<210> SEQ ID NO 105
<211> LENGTH: 76
<212> TYPE: DNA
<213> ORGANISM: Artificial Sequence
<220> FEATURE:
```

-continued

```
<223> OTHER INFORMATION: Description of Artificial Sequence:top strand
      complementary oligonucleotide

<400> SEQUENCE: 105
ggccgcgaac aaaaactcat ctcagaagag gatctgggtg gtgagcagaa gttgatttct        60
gaggaagacc tgggcc                                                        76

<210> SEQ ID NO 106
<211> LENGTH: 68
<212> TYPE: DNA
<213> ORGANISM: Artificial Sequence
<220> FEATURE:
<223> OTHER INFORMATION: Description of Artificial Sequence:bottom
      strand complementary oligonucleotide

<400> SEQUENCE: 106
caggtcttcc tcagaaatca acttctgctc accacccaga tcctcttctg agatgagttt        60
ttgttcgc                                                                 68

<210> SEQ ID NO 107
<211> LENGTH: 47
<212> TYPE: DNA
<213> ORGANISM: Artificial Sequence
<220> FEATURE:
<223> OTHER INFORMATION: Description of Artificial Sequence:3' primer

<400> SEQUENCE: 107
tagactcgag cggccgccct cttggttgta gcggccaggc atgatcc                      47
```